US008728724B2

(12) United States Patent
Williams et al.

(10) Patent No.: US 8,728,724 B2
(45) Date of Patent: May 20, 2014

(54) IDENTIFICATION OF MICRO-RNAS INVOLVED IN NEUROMUSCULAR SYNAPSE MAINTENANCE AND REGENERATION

(75) Inventors: Andrew Williams, Richardson, TX (US); Eric Olson, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 13/525,657

(22) Filed: Jun. 18, 2012

(65) Prior Publication Data
US 2013/0030035 A1   Jan. 31, 2013

Related U.S. Application Data

(63) Continuation of application No. 12/405,859, filed on Mar. 17, 2009, now Pat. No. 8,202,848.

(60) Provisional application No. 61/037,260, filed on Mar. 17, 2008.

(51) Int. Cl.
 *C12Q 1/68*   (2006.01)
 *C07H 21/02*  (2006.01)
 *C07H 21/04*  (2006.01)

(52) U.S. Cl.
 USPC .......... 435/6; 435/91.1; 435/91.31; 536/23.1; 536/24.31; 536/24.5

(58) Field of Classification Search
 USPC .......... 435/6, 6.1, 6.11, 91.1, 91.31; 514/1, 2, 514/44; 536/23.1, 24.3, 24.5, 24.31
 See application file for complete search history.

(56) References Cited

U.S. PATENT DOCUMENTS

| | | | |
|---|---|---|---|
| 5,994,315 A | 11/1999 | Nyce et al. | |
| 6,025,339 A | 2/2000 | Nyce | |
| 6,040,296 A | 3/2000 | Nyce | |
| 6,825,174 B2 | 11/2004 | Nyce | |
| 7,034,007 B1 | 4/2006 | Nyce et al. | |
| 7,229,774 B2 | 6/2007 | Chinnaiyan et al. | |
| 7,232,806 B2 | 6/2007 | Tuschl et al. | |
| 7,390,792 B2 | 6/2008 | Srivastava et al. | |
| 7,482,117 B2 | 1/2009 | Cargill et al. | |
| 7,718,630 B2 | 5/2010 | Srivastava et al. | |
| 7,723,510 B1 | 5/2010 | Tuschl et al. | |
| 8,202,848 B2 * | 6/2012 | Williams et al. ............ 514/44 R |
| 2003/0087845 A1 | 5/2003 | Nyce | |
| 2003/0175736 A1 | 9/2003 | Chinnaiyan et al. | |
| 2005/0014711 A1 | 1/2005 | Nyce | |
| 2005/0026169 A1 | 2/2005 | Cargill et al. | |
| 2005/0059005 A1* | 3/2005 | Tuschl et al. .................. 435/6 |
| 2005/0074788 A1 | 4/2005 | Dahlberg et al. | |
| 2005/0182005 A1* | 8/2005 | Tuschl et al. .................. 514/44 |
| 2005/0261218 A1 | 11/2005 | Esau et al. | |
| 2005/0266418 A1 | 12/2005 | Chen et al. | |
| 2006/0019286 A1 | 1/2006 | Horvitz et al. | |
| 2006/0105360 A1* | 5/2006 | Croce et al. .................. 435/6 |
| 2006/0185027 A1 | 8/2006 | Bartel et al. | |
| 2006/0246491 A1 | 11/2006 | Srivastava | |
| 2006/0247193 A1 | 11/2006 | Taira et al. | |
| 2006/0252722 A1 | 11/2006 | Lollo et al. | |
| 2006/0265771 A1 | 11/2006 | Lewis et al. | |
| 2007/0003939 A1 | 1/2007 | Wang et al. | |
| 2007/0050146 A1 | 3/2007 | Bentwich et al. | |
| 2007/0054872 A1 | 3/2007 | Reppen et al. | |
| 2007/0065840 A1 | 3/2007 | Naguibneva et al. | |
| 2007/0065844 A1 | 3/2007 | Golub et al. | |
| 2007/0092882 A1 | 4/2007 | Wang et al. | |
| 2007/0099196 A1 | 5/2007 | Kauppinen et al. | |
| 2007/0142313 A1 | 6/2007 | Srivastava et al. | |
| 2007/0161004 A1* | 7/2007 | Brown et al. .................. 435/6 |
| 2008/0124737 A1 | 5/2008 | Srivastava et al. | |
| 2008/0176766 A1 | 7/2008 | Brown et al. | |
| 2009/0004668 A1* | 1/2009 | Chen et al. .................. 435/6 |
| 2009/0005336 A1 | 1/2009 | Wang | |
| 2009/0010908 A1* | 1/2009 | Gow et al. .................. 424/94.1 |
| 2009/0053718 A1 | 2/2009 | Naguibneva et al. | |
| 2009/0092980 A1 | 4/2009 | Arenz et al. | |
| 2009/0130751 A1 | 5/2009 | Davidson et al. | |
| 2009/0143326 A1 | 6/2009 | Obad et al. | |
| 2009/0176723 A1 | 7/2009 | Brown et al. | |
| 2009/0186414 A1 | 7/2009 | Srivastava et al. | |
| 2009/0209626 A1 | 8/2009 | Khvorova et al. | |
| 2009/0215865 A1 | 8/2009 | Plasterk et al. | |
| 2009/0286969 A1 | 11/2009 | Esau et al. | |
| 2009/0291906 A1 | 11/2009 | Esau et al. | |
| 2009/0291907 A1 | 11/2009 | Esau et al. | |
| 2009/0293148 A1 | 11/2009 | Ren et al. | |

(Continued)

FOREIGN PATENT DOCUMENTS

| | | |
|---|---|---|
| EP | 1627925 A1 | 2/2006 |
| EP | 1777301 A2 | 4/2007 |
| EP | 1959012 A2 | 8/2008 |
| EP | 2105145 A1 | 9/2009 |
| EP | 2194129 A2 | 6/2010 |
| EP | 2208798 A1 | 7/2010 |
| JP | 2006-292367 | 10/2006 |
| WO | WO 96/40162 A1 | 12/1996 |
| WO | WO 96/40266 A1 | 12/1996 |
| WO | WO 98/23294 A1 | 6/1998 |

(Continued)

OTHER PUBLICATIONS

Doench et al., Genes & Development, vol. 18, No. 5, pp. 504-511 (2004).*
Holen et al., Nucleic Acids Res., vol. 30, No. 8, pp. 1757-1766 (2002).*
Opalinska et al., Nature Rev., vol. 1, pp. 503-514 (2002).*
Peracchi et al., Rev. Med. Virol., vol. 14, pp. 47-64 (2004).*
McCarthy, "MicroRNA-206: The Skeletal Muscle-Specific MyomiR," *Biochim. Biophy. Acta.* Mar. 12, 2008 1779:682-691.

(Continued)

*Primary Examiner* — Jane Zara
(74) *Attorney, Agent, or Firm* — Cooley LLP

(57) ABSTRACT

The present invention relates to the identification of miRNAs that are involved in the process of neuromuscular synaptic maintenance and regeneration following injury or disease. Modulation of these miRNAs is proposed as treatment for spinal cord injury and neurodegenerative disease.

16 Claims, 10 Drawing Sheets

(56) References Cited

U.S. PATENT DOCUMENTS

| | | |
|---|---|---|
| 2009/0298916 A1 | 12/2009 | Kauppinen et al. |
| 2009/0317369 A1 | 12/2009 | Hosoda et al. |
| 2010/0010073 A1 | 1/2010 | Thum et al. |
| 2010/0029003 A1 | 2/2010 | Bartel et al. |
| 2010/0087512 A1 | 4/2010 | Tuschl et al. |
| 2010/0087513 A1 | 4/2010 | Tuschl et al. |
| 2010/0093837 A1 | 4/2010 | Tuschl et al. |
| 2010/0099748 A1 | 4/2010 | Tuschl et al. |
| 2010/0113561 A1 | 5/2010 | Tuschl et al. |
| 2010/0173288 A1 | 7/2010 | Zhang et al. |
| 2010/0173973 A1 | 7/2010 | Brown et al. |
| 2010/0173974 A1 | 7/2010 | Brown et al. |
| 2010/0292297 A1* | 11/2010 | Wang et al. .............. 514/44 A |
| 2013/0017972 A1* | 1/2013 | Brown et al. .............. 506/9 |

FOREIGN PATENT DOCUMENTS

| | | |
|---|---|---|
| WO | WO 99/13886 A1 | 3/1999 |
| WO | WO 99/63938 A2 | 12/1999 |
| WO | WO 02/44321 * | 6/2002 |
| WO | WO 03/029459 A2 | 4/2003 |
| WO | WO 2004/076622 A2 | 9/2004 |
| WO | WO 2005/013901 A2 | 2/2005 |
| WO | WO 2005/019433 A2 | 3/2005 |
| WO | WO 2005/040419 A1 | 5/2005 |
| WO | WO 2005/078139 A2 | 8/2005 |
| WO | WO 2005/079397 A2 | 9/2005 |
| WO | WO 2005/085280 A2 | 9/2005 |
| WO | WO 2005/103298 A2 | 11/2005 |
| WO | WO 2005/118806 A2 | 12/2005 |
| WO | WO 2006/015389 A2 | 2/2006 |
| WO | WO 2006/025879 A2 | 3/2006 |
| WO | WO 2006/047454 A2 | 3/2006 |
| WO | WO 2006/069584 A2 | 7/2006 |
| WO | WO 2006/081284 A2 | 8/2006 |
| WO | WO 2006/107826 A2 | 10/2006 |
| WO | WO 2006/108473 A1 | 10/2006 |
| WO | WO 2006/111512 A1 | 10/2006 |
| WO | WO 2006/119266 A2 | 11/2006 |
| WO | WO 2006/133022 A2 | 12/2006 |
| WO | WO 2006/137941 A2 | 12/2006 |
| WO | WO 2007/000668 A2 | 1/2007 |
| WO | WO 2007/002375 A2 | 1/2007 |
| WO | WO 2007/016548 A2 | 2/2007 |
| WO | WO 2007/028030 A2 | 3/2007 |
| WO | WO 2007/033023 A2 | 3/2007 |
| WO | WO 2007/042899 A2 | 4/2007 |
| WO | WO 2007/070483 A2 | 6/2007 |
| WO | WO 2007/073737 A1 | 7/2007 |
| WO | WO 2007/081196 A1 | 7/2007 |
| WO | WO 2007/081680 A2 | 7/2007 |
| WO | WO 2007/103808 A2 | 9/2007 |
| WO | WO 2007/112754 A2 | 10/2007 |
| WO | WO 2008/015028 A1 | 2/2008 |
| WO | WO 2008/042231 A2 | 4/2008 |
| WO | WO 2008/043521 A2 | 4/2008 |
| WO | WO 2008/061537 A2 | 5/2008 |
| WO | WO 2008/147430 A2 | 12/2008 |
| WO | WO 2008/147839 A1 | 12/2008 |
| WO | WO 2008/150897 A2 | 12/2008 |
| WO | WO 2009/026576 A1 | 2/2009 |
| WO | WO 2009/043353 A2 | 4/2009 |
| WO | WO 2009/111375 A2 | 9/2009 |
| WO | WO 2009/134710 A2 | 11/2009 |
| WO | WO 2009/149182 A1 | 12/2009 |
| WO | WO 2010/036111 A1 | 4/2010 |
| WO | WO 2010/048585 A2 | 4/2010 |

OTHER PUBLICATIONS

Liu et al., "An Intragenic MEF2-Dependent Enhancer Directs Muscle-Specific Expression of MicroRNAs 1 and 133." *Proc. Natl. Acad. Sci. USA* Dec. 26, 2007, 104(52):20844-20849.

Biemar et al., "Spatial Regulation of MicroRNA Gene Expression in the *Drosophila* Embryo." *Proc. Natl. Acad. Sci. USA* Nov. 1, 2005, 102(44):15907-15911.

Rao et al., "Myogenic Factors That Regulate Expression of Muscle-Specific MicroRNAs", *Proc. Natl. Acad. Sci. USA* Jun. 6, 2006, 103(23):8721-8726.

International Search Report and Written Opinion based on International Application PCT/US2009/037405 (Oct. 16, 2009).

Chen et al., "The Role of MicroRNA-1 and MicroRNA-133 in Skeletal Muscle Proliferation and Differentiation," *Nature Genetics*, vol. 38(2): 228-233, 2006.

McCARTHY et al., "MicroRNA-206 is overexpressed in the diaphragm but not the hindlimb of mdx mouse," *Amer. Journal of Physiol. Cell Physiology*, vol. 293:C451-C457, 2007.

Williams et al., "MicroRNA-206 Delays ALS Progression and Promotes Regeneration of Neuromuscular Synapses in Mice," *Science*, vol. 326: 1549-1554, 2009.

Greco et al., "Common micro-RNA signature in skeletal muscle damage and regeneration induced by Duchenne muscular dystrophy and acute ischemia," *FASEB J.*, vol. 23: 3335-3346, 2009.

Piret, European Supplementary Search Report and Opinion for European Application No. EP 09721861.4 mailed Aug. 30, 2012 (10 pages).

* cited by examiner

FIGURE 2A-D
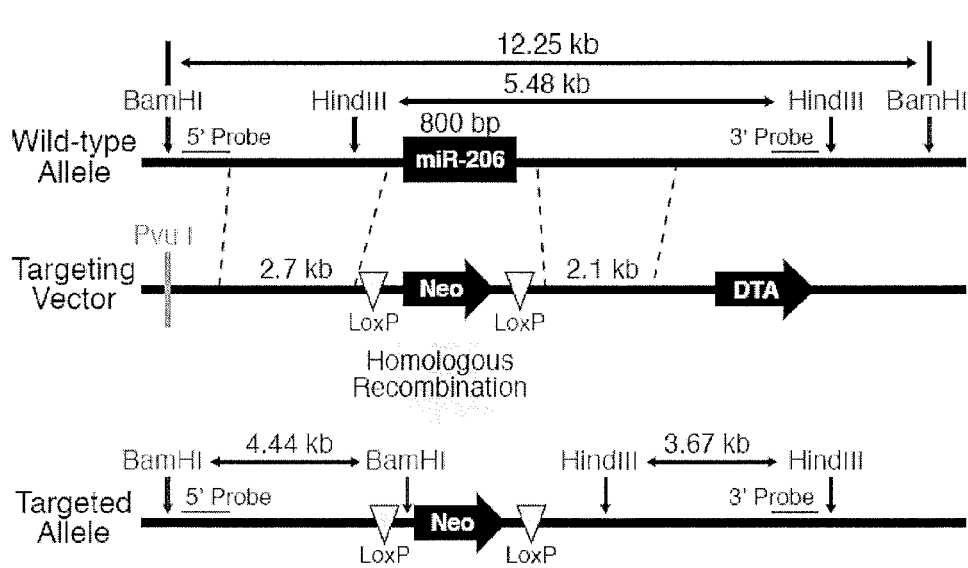
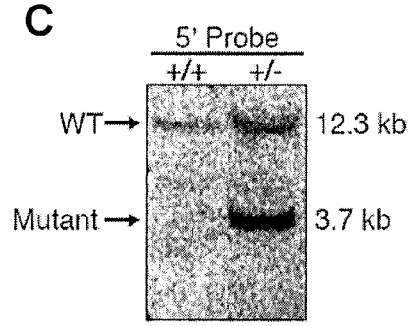
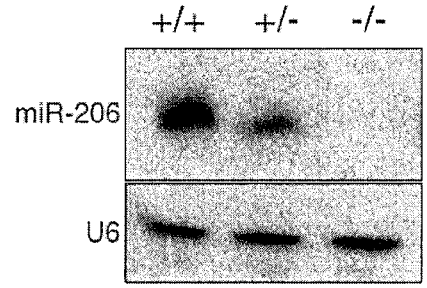

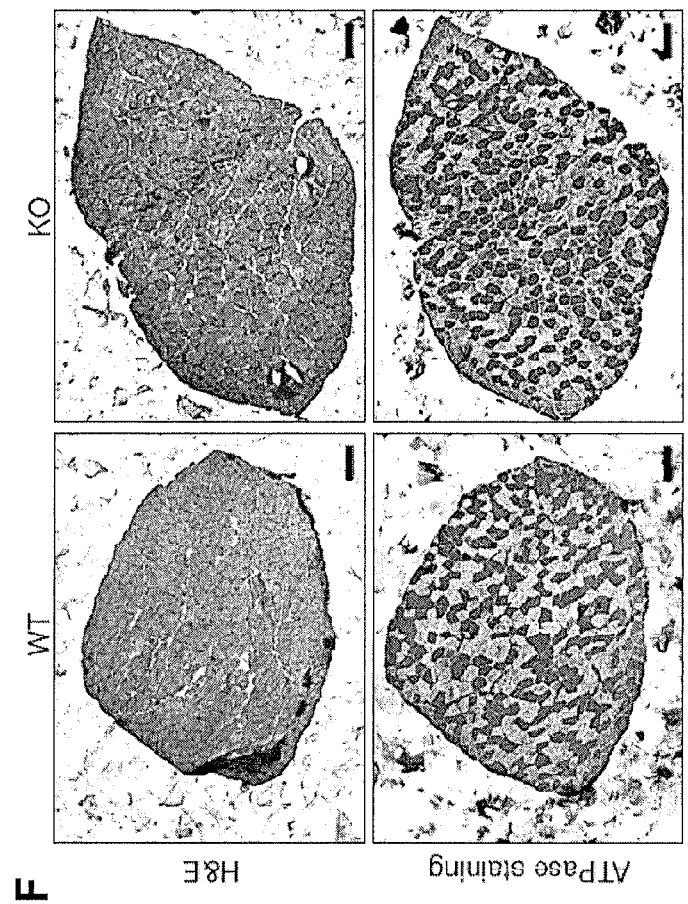
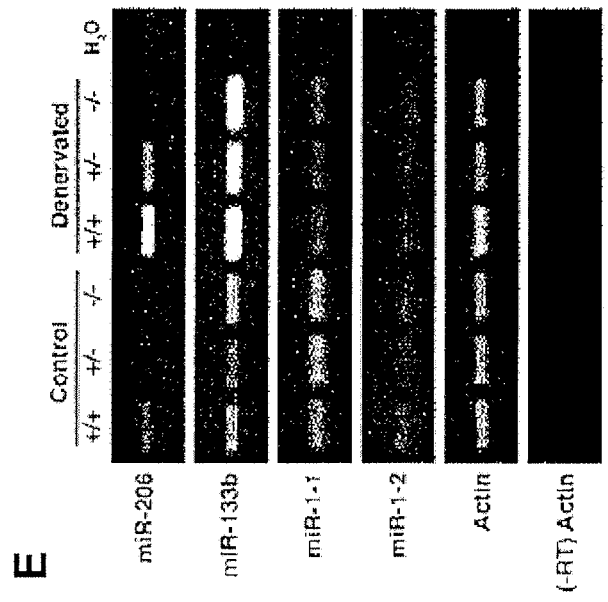
FIGURE 2E-F

FIGURE 3A-B
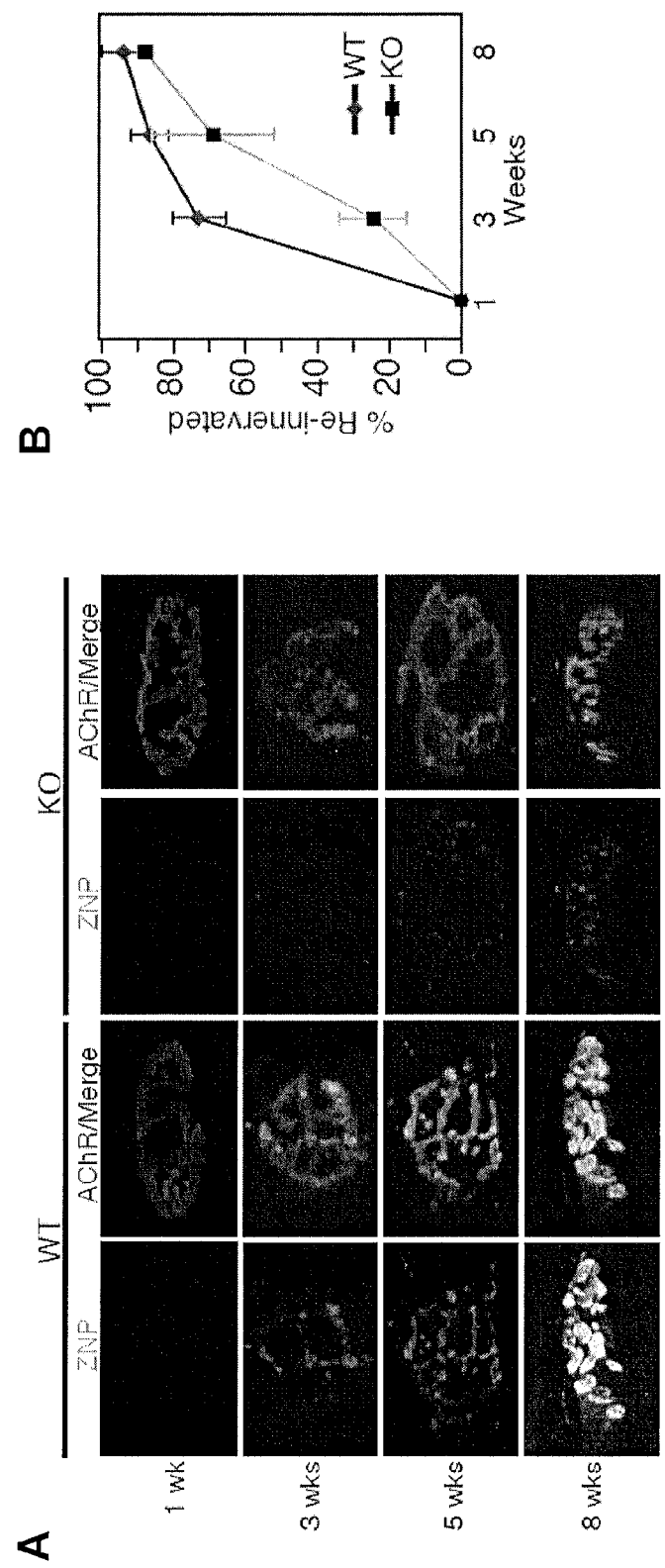

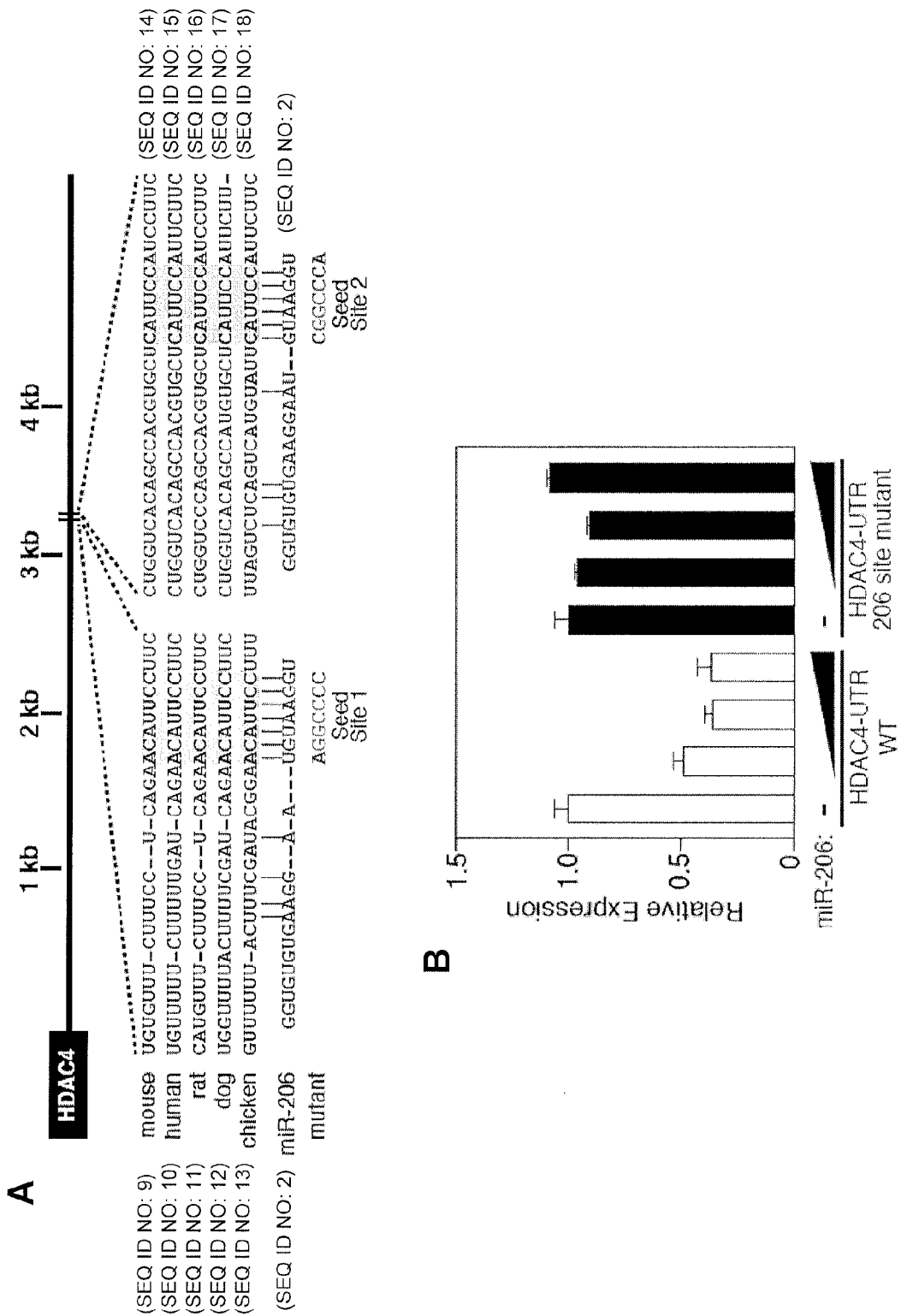
FIGURE 4A-B

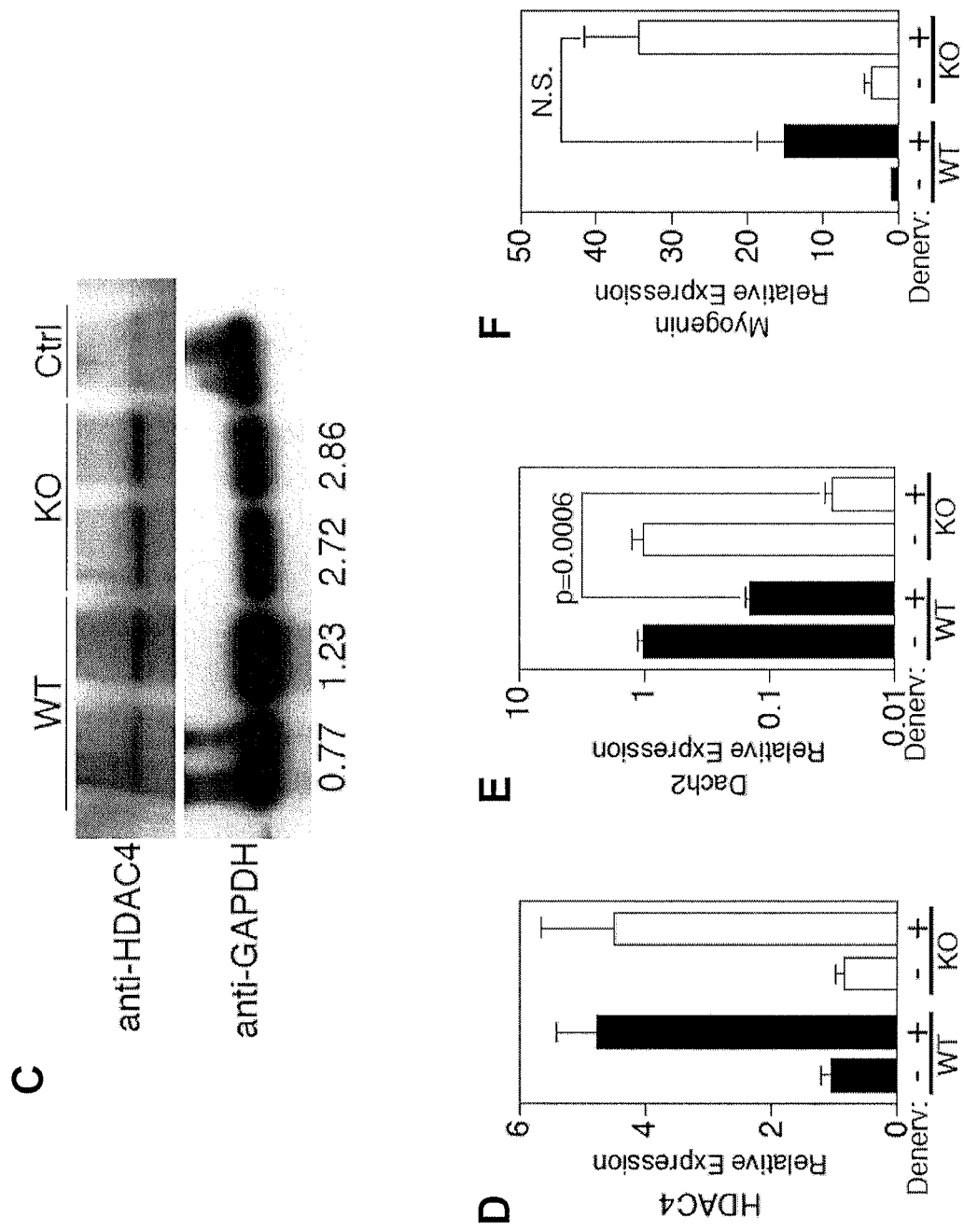
FIGURE 4C-F

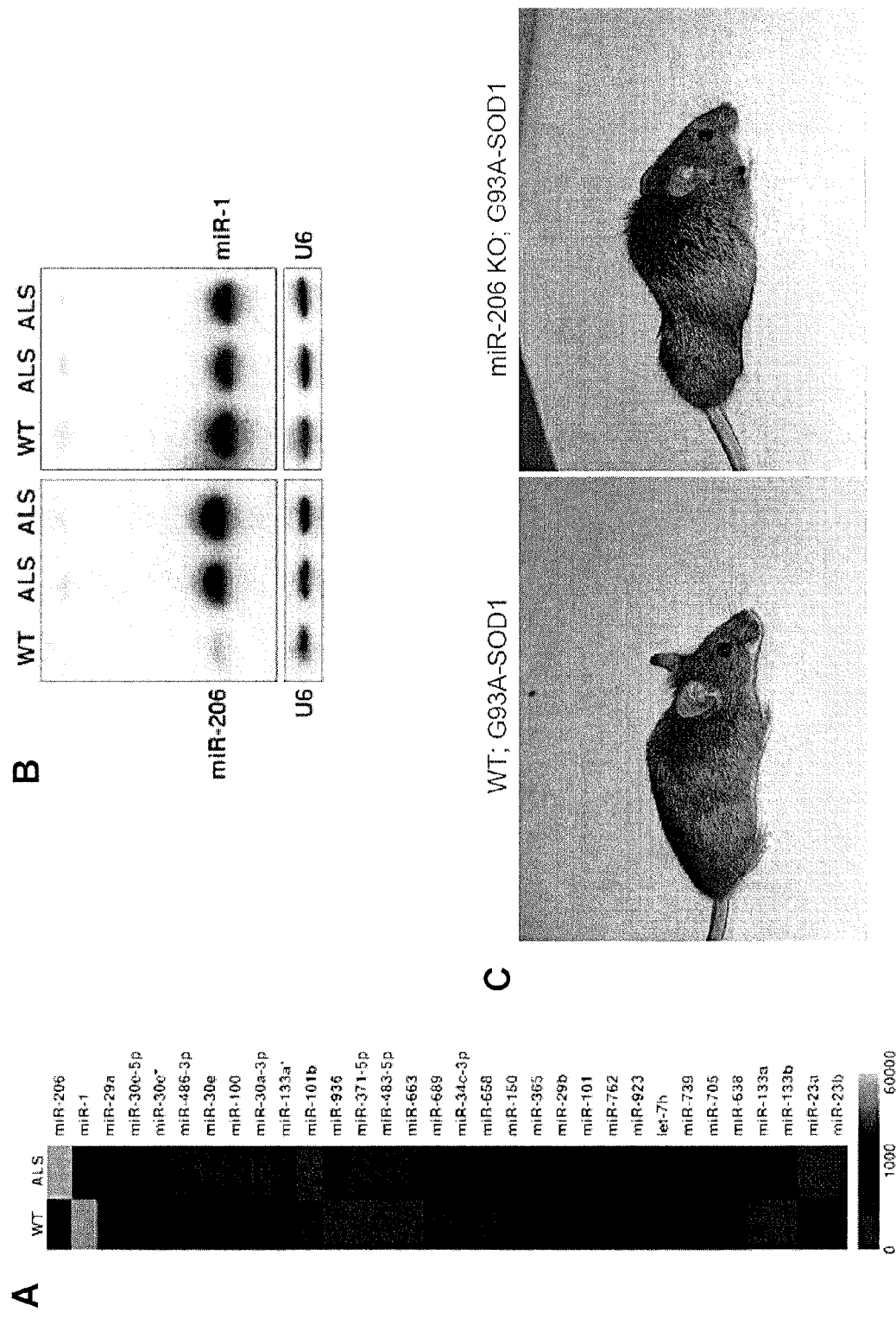
FIGURE 5A-C

SEQUENCE LISTING

<160> NUMBER OF SEQ ID NOS: 18

<210> SEQ ID NO 1
<211> LENGTH: 86
<212> TYPE: RNA
<213> ORGANISM: Homo sapiens

<400> SEQUENCE: 1
ugcuucccga ggccacaugc uucuuuauau ccccauaugg auuacuuugc uauggaaugu    60
aaggaagugu gugguuucgg caagug    86

<210> SEQ ID NO 2
<211> LENGTH: 22
<212> TYPE: RNA
<213> ORGANISM: Homo sapiens

<400> SEQUENCE: 2
uggaauguaa ggaagugugu gg    22

<210> SEQ ID NO 3
<211> LENGTH: 85
<212> TYPE: RNA
<213> ORGANISM: Homo sapiens

<400> SEQUENCE: 3
accuacucag aguacauacu ucuuuaugua cccauaugaa cauacaaugc uauggaaugu    60
aaagaaguau guauuuuugg uaggc    85

<210> SEQ ID NO 4
<211> LENGTH: 22
<212> TYPE: RNA
<213> ORGANISM: Homo sapiens

```
<400> SEQUENCE: 4
uggaauguaa agaaguaugu au                                            22

<210> SEQ ID NO 5
<211> LENGTH: 88
<212> TYPE: RNA
<213> ORGANISM: Homo sapiens

<400> SEQUENCE: 5
acaaugcuuu gcuagagcug guaaaaugga accaaaucgc cucuucaaug gauuuggucc   60
ccuucaacca gcuguagcua ugcauuga                                     88

<210> SEQ ID NO 6
<211> LENGTH: 22
<212> TYPE: RNA
<213> ORGANISM: Homo sapiens

<400> SEQUENCE: 6
uuuggucccc uucaaccagc ug                                            22

<210> SEQ ID NO 7
<211> LENGTH: 119
<212> TYPE: RNA
<213> ORGANISM: Homo sapiens

<400> SEQUENCE: 7
ccucagaaga aagaugcccc cugcucuggc uggucaaacg gaaccaaguc cgucuuccug   60
agagguuugg uccccuucaa ccagcuacag cagggcuggc aaugcccagu ccuuggaga  119

<210> SEQ ID NO 8
<211> LENGTH: 22
<212> TYPE: RNA
<213> ORGANISM: Homo sapiens

<400> SEQUENCE: 8
uuuggucccc uucaaccagc ua                                            22

<210> SEQ ID NO 9
<211> LENGTH: 28
<212> TYPE: RNA
<213> ORGANISM: Mus sp.

<400> SEQUENCE: 9
uguguuucuu uccucagaac auuccuuc                                      28

<210> SEQ ID NO 10
<211> LENGTH: 30
<212> TYPE: RNA
<213> ORGANISM: Homo sapiens

<400> SEQUENCE: 10
uguuuuucuu uuugaucaga acauuccuuc                                    30

<210> SEQ ID NO 11
<211> LENGTH: 28
<212> TYPE: RNA
<213> ORGANISM: Rattus sp.

<400> SEQUENCE: 11
cauguuucuu uccucagaac auuccuuc                                      28
```

```
<210> SEQ ID NO 12
<211> LENGTH: 31
<212> TYPE: RNA
<213> ORGANISM: Canis sp.

<400> SEQUENCE: 12
ugguuuuacu uuucgaucag aacauuccuu c                              31

<210> SEQ ID NO 13
<211> LENGTH: 31
<212> TYPE: RNA
<213> ORGANISM: Gallus sp.

<400> SEQUENCE: 13
guuuuuuacu uucgauacgg aacauuccuu u                              31

<210> SEQ ID NO 14
<211> LENGTH: 32
<212> TYPE: RNA
<213> ORGANISM: Mus sp.

<400> SEQUENCE: 14
cuggucacag ccacgugcuc auuccauccu uc                             32

<210> SEQ ID NO 15
<211> LENGTH: 32
<212> TYPE: RNA
<213> ORGANISM: Homo sapiens

<400> SEQUENCE: 15
cuggucacag ccacgugcuc auuccauucu uc                             32

<210> SEQ ID NO 16
<211> LENGTH: 32
<212> TYPE: RNA
<213> ORGANISM: Rattus sp.

<400> SEQUENCE: 16
cuggucccag ccacgugcuc auuccauccu uc                             32

<210> SEQ ID NO 17
<211> LENGTH: 31
<212> TYPE: RNA
<213> ORGANISM: Canis sp.

<400> SEQUENCE: 17
cuggucacag ccaugugcuc auuccauucu u                              31

<210> SEQ ID NO 18
<211> LENGTH: 32
<212> TYPE: RNA
<213> ORGANISM: Gallus sp.

<400> SEQUENCE: 18
uuagucucag ucauguauuc auuccauucu uc                             32
```

IDENTIFICATION OF MICRO-RNAS INVOLVED IN NEUROMUSCULAR SYNAPSE MAINTENANCE AND REGENERATION

CROSS-REFERENCE TO RELATED APPLICATIONS

This application is a continuation of U.S. application Ser. No. 12/405,859, filed on Mar. 17, 2009, which claims the benefit of U.S. Provisional Application No. 61/037,260, filed Mar. 17, 2008, each of which is herein incorporated by reference in its entirety.

STATEMENT OF GOVERNMENT SUPPORT

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_12_02US_SeqList_ST25.txt, date recorded: Oct. 1, 2012, file size 4 kilobytes).

FIELD OF THE INVENTION

The present invention relates generally to the fields of developmental biology, neurobiology, pathology and molecular biology. More particularly, it concerns altered miRNA expression in skeletal muscle tissues that impacts neuromuscular synaptic maintenance and regeneration in injury or disease. The invention provides methods of treating a subject afflicted with a denervating disease by administering agonists of particular miRNAs (e.g. miR-206 and miR-1).

BACKGROUND OF THE INVENTION

Amyotrophic lateral sclerosis (ALS), familiarly known as Lou Gehrig's disease, is the most common adult motor neuron disease, affecting approximately 30,000 persons in the United States (Bruijn et al., 2004). About 90% of ALS cases are sporadic and the other 10% occur as a result of an inherited mutation (Boillee et al., 2006). Regardless of the manner in which ALS is acquired, similar symptoms characterize the progression of the disease. The symptoms include the denervation of target skeletal muscles through the selective loss and degeneration of motor neurons, which leads to muscle atrophy and paralysis in the limbs and respiratory muscles. Although ALS is the most common motor neuron disease, there is no cure or effective treatment that can prevent the loss of motor neurons or significantly improve survival after diagnosis. The identification of signaling pathways and downstream molecules that regulate the initiation and progression of ALS remains a significant challenge in the search for novel therapeutics (Dunckley et al., 2007).

The transcriptional and post-translational regulatory networks that control neuromuscular synapse assembly and maintenance have been well characterized (Sanes and Lichtman, 2001); however, a role for post-transcriptional mechanisms in regulating this process has not been described. In this regard, microRNAs (miRNAs or miRs) are being recognized as major post-transcriptional regulators of many biological processes (Bartel, 2004; Van Rooij et al., 2007a). mRNAs are small, non-protein coding RNAs of about 18 to about 25 nucleotides in length that regulate gene expression in a sequence-specific manner. mRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) Cellular & Molecular Immunology Vol. 3:411-419) and arise from initial transcripts, termed primary miRNA transcripts (pri-miRNAs), that are generally several thousand bases long and are derived from individual miRNA genes, from introns of protein coding genes, or from poly-cistronic transcripts that often encode multiple, closely related miRNAs. See review of Carrington et al. (2003). Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA (Lee et al., 1993). The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation. Loss of function mutations in vertebrates have demonstrated that miRNAs are key regulators of diverse biological processes including cardiac hypertrophy, heart morphogenesis, and lymphocyte development (Van Rooij et al., 2007b; Zhao et al., 2007; Xiao et al., 2007). However, the relationship of miRNAs to neuromuscular synapse function and signaling remains to be established.

SUMMARY OF THE INVENTION

The present invention is based, in part, on the discovery that miR-206 regulates neuromuscular junction stability and regeneration following denervation as a result of injury or neurodegenerative disease. Accordingly, the present invention provides a method of treating a subject afflicted with a denervating neuropathic state. In one embodiment, the method comprises administering to the subject an agonist of miR-206 and/or miR-1. In another embodiment, the agonist is a polynucleotide comprising a mature sequence of miR-206 and/or miR-1. In another embodiment, the agonist is encoded by an expression vector. The denervating neuropathic state can be spinal cord injury, myasthenia gravis, amyotrophic lateral sclerosis, Friedreich's ataxia, spinal muscular atrophy, or spinocerebellar ataxia.

The present invention also includes a method for diagnosing a denervating neuropathic state (e.g. spinal cord injury or ALS) in a subject. In one embodiment, the method comprises (a) obtaining a skeletal muscle tissue sample from the subject; (b) assessing activity or expression of miR-206 and/or miR-133b in said sample; and (c) comparing the activity or expression in step (b) with the activity or expression of miR-206 and/or miR-133b in a normal tissue sample, wherein an increase in the activity or expression of miR-206 and/or miR-133b as compared to the activity or expression of miR-206 and/or miR-133b in a normal tissue sample is diagnostic of a denervating neuropathic state. Assessing miR-206 and/or miR-133b activity can comprise assessing the activity of one or more genes regulated by miR-206 and/or miR-133b. In one embodiment, the one or more genes regulated by miR-206 are selected from the group consisting of HDAC4, Dach2, or myogenin.

The present invention also provides a method for identifying a modulator of miR-206 and/or miR-1 activity in skeletal muscle. In one embodiment, the method comprises (a) contacting a skeletal muscle cell with a candidate compound; (b) assessing miR-206 and/or miR-1 activity or expression; and (c) comparing the activity or expression in step (b) with the activity or expression in the absence of the candidate compound, wherein a difference between the measured activities or expression indicates that the candidate compound is a modulator of miR-206 and/or miR-1. The cell may be contacted with the candidate compound in vitro or in vivo. The modulator of miR-206 and/or miR-1 may be an agonist of miR-206 and/or miR-1 or an inhibitor of miR-206 and/or miR-1.

The present invention also encompasses a pharmaceutical composition comprising an agonist of miR-206 and/or miR-1 and a pharmaceutically acceptable carrier. In some embodiments, the pharmaceutical composition may be administered with a second therapy for a denervating neuropathic state.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(A) Northern blot analysis showing skeletal muscle specific expression of mature miR-206 in adult mouse tissues. The northern blot was re-probed with U6 as a loading control. (B) Northern blot analysis of miR-1 and miR-206 expression in adult mouse muscle tissues 10-days after sciatic nerve transection. The contra-lateral leg was used as a control. Northern blots were re-probed with U6 as a loading control. EDL=extensor digitorum longus, TA=tibialis anterior, GP=gastrocnemius/plantaris. (C) Transcripts of miR-206, miR-133b, miR-1, and miR-133a were detected by real time PCR in TA muscles following 10-days of denervation (+). The contra-lateral muscle was used as a control (−).

FIG. 2. Generation of miR-206 Mutant Mice.

(A) Diagram of the miR-206/133b murine locus. (B) Targeting strategy to delete miR-206 from the miR-206/133b locus by replacing the pre-miR-206 sequence with a neomycin cassette flanked by loxP sites. Positions of 5' and 3' probes used for Southern blots are shown. (C) Southern blot analysis of genomic DNA from wild-type and heterozygous mice using an external 5' probe. Genomic DNA was digested with BamHI. (D) Northern blot analysis of mature miR-206 transcript expression in gastrocnemius/plantaris muscle of the indicated miR-206 genotypes. U6 was used as loading control. (E) RT-PCR using gene specific primers for pre-miR-206, pre-miR-133b, pre-miR-1-1, and pre-miR-1-2 in the soleus muscle of control and miR-206 mutant mice after denervation. (F) Hematoxylin and eosin (H&E) and metachromatic ATPase staining show no difference in the skeletal muscle architecture and distribution of Type I (dark blue) and Type II (light blue) skeletal myofibers in the soleus muscles of wild-type (WT) and miR-206−/− (KO) mice.

FIG. 3. Delayed Reinnervation in miR-206 Mutant Mice.

(A) Following sciatic nerve transection (as indicated in weeks), a delay in reinnervation is observed in miR-206−/− (KO) mice compared to wild-type (WT) mice as detected by the superimposition of anti-ZNP staining (green) with BTX (red). Note the lack of anti-ZNP (green) staining in miR-206−/− mice. (B) Time course and quantification of the number of reinnervated synaptic sites in WT and miR-206 KO mice following sciatic nerve transection. (C) Immunohistochemistry using BTX (red) and anti-ZNP (green) shows a delay in reinnervation of NMJs in miR-206−/− mice compared to WT mice following 7 and 18 days after nerve crush. Note the lack of anti-ZNP (green) staining in miR-206−/− mice.

Figure 4G:
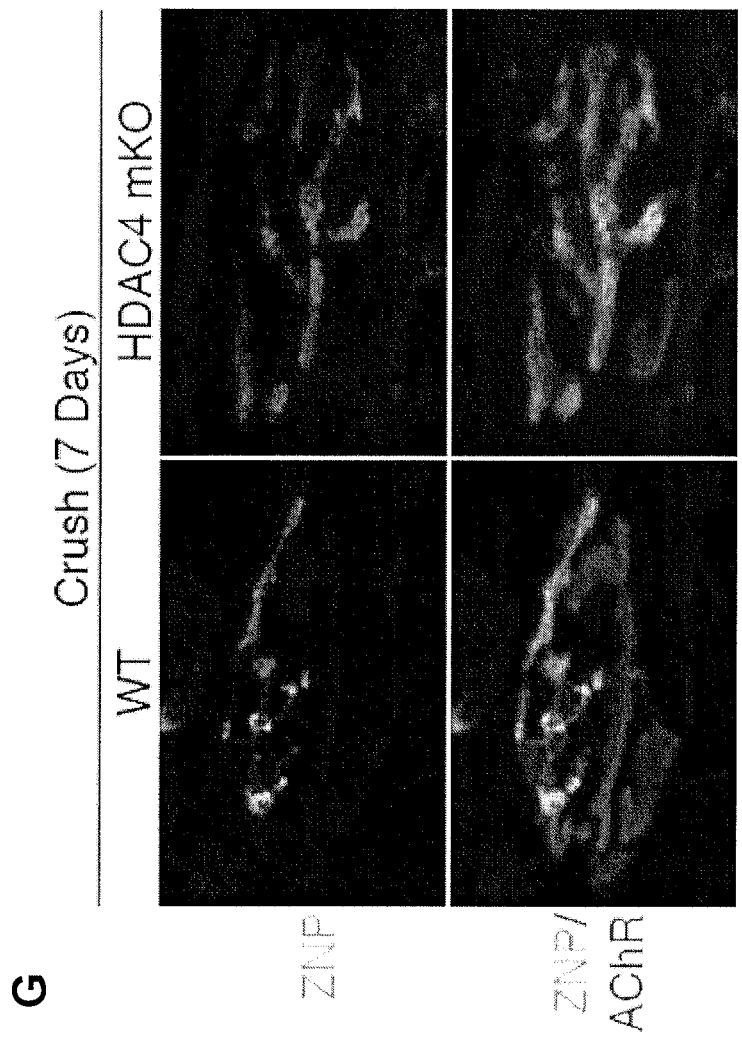

FIG. 4. MiR-206 Targets HDAC4.

(A) Schematic diagram of the Hdac4 3' UTR from several species with sequence homologies of the two predicted miR-206 binding sites. (B) Luciferase activity of COS1 cells co-transfected with wild-type (WT) or mutant HDAC4 3'UTR-luciferase constructs with increasing amounts of miR-206 expression plasmid. Mutation of the predicted miR-206 binding sites in the 3'UTR alleviates the inhibitory activity of miR-206. Values are normalized to β-galactosidase activity. (C) Western blot analysis showing increased HDAC4 expression in muscle lysates isolated from wild-type (WT) and miR-206−/− (KO) mice 3-weeks following denervation. Control (Ctrl.) refers to HDAC4 mKO protein lysate. GAPDH protein was detected as a control. Relative protein expression compared to WT is indicated below the blot. (D) Transcripts of Hdac4 were detected in wild-type (WT) and miR-206−/− (KO) muscles after 3-weeks of denervation. (E) Transcripts of Dach2 were detected in wild-type (WT) and miR-206−/− (KO) muscles after 3-weeks of denervation. (F) Transcripts of myogenin were detected in wild-type (WT) and miR-206−/− (KO) TA muscles after 3-weeks of denervation. (G) Immunohistochemistry using BTX (red) and anti-ZNP (green) shows an increase in reinnervation in HDAC4 mKO mutant mice compared to WT mice 7 days following nerve crush. Note the increase in anti-ZNP (green) staining in HDAC4 mKO mice.

FIG. 5. Upregulation of miR-206 in ALS Mice.

(A) Heat plot of miRNA array profiling of miRNAs in wild-type (WT) and G93A-SOD1 (ALS) mice. (B) Northern blot analysis of miR-1 and miR-206 expression in 7-month old wild-type (WT) and G93A-SOD1 (ALS) TA muscles. Northern blots were re-probed with U6 as a loading control. (C) ALS pathogenesis is increased in miR-206/G93A-SOD1 double mutant mice. Representative image of a G93A-SOD1 mouse and a miR-206/G93A-SOD1 double mutant mouse. (D) Muscle degeneration is increased in miR-206/G93A-SOD1 double mutant mice. Hematoxylin and eosin (H&E) staining of gastrocnemius/plantaris muscles of wild-type (WT), miR-206 mutant, G93A-SOD1, and miR-206/G93A-SOD1 double mutant mice.

DETAILED DESCRIPTION

The present invention is based, in part, on the discovery that miR-206 regulates neuromuscular junction stability and regeneration following injury. MiR-206 is upregulated in skeletal muscles of a mouse model of ALS and in response to denervation following nerve transection or crush. In addition, the related molecule, miR-133b, is upregulated in a similar fashion to miR-206, while miR-1 and miR-133a exhibit a reduced expression in the ALS disease model and in response to surgical denervation. Through the creation of miR-206 null mice, the inventors established an essential role for miR-206 in regulating neuromuscular junction stability and regeneration following injury. These results describe the first role of an miRNA in regulating neuromuscular synapse function, and point to miR-206 and miR-1 as key components in pathogenesis of ALS and other denervating diseases and injuries. Accordingly, the present invention provides novel therapeutic approaches for treating neurodegenerative diseases and nerve damage by manipulating expression levels of miR-206 and/or miR-1.

In vertebrates, three pairs of muscle-specific miRNAs, miR-1-1/133a-2, miR-1-2/133a-1, and miR-206/133b are transcribed as bicistronic transcripts on separate chromosomes (Liu et al., 2007). MiR-1 has been shown to regulate cardiac myocyte proliferation and heart morphogenesis through the repression of the transcription factor, Hand2 (Zhao et al., 2005; 2007). In skeletal myoblasts, miR-1 was shown to promote differentiation through the repression of histone deacetylase 4 (EIDAC4), a repressor of myogenesis; paradoxically, miR-133 was shown to repress differentiation through the repression of serum response factor (SRF), an activator of myogenesis (Chen et al., 2006). MiR-1-1 is co-transcribed with miR-133a-2 from human chromosome 20, while miR-1-2 is co-transcribed with miR-133a-1 from human chromosome 18. In addition, miR-206, an evolutionarily divergent member of the miR-1 family of miRNAs, has been shown to promote myoblast differentiation through the repression of various target genes, including a subunit of the DNA polymerase α (Polα), connexin 43 (Cx43), follistatin-like 1 (Fstll), and utrophin (Utrn) (Kim et al., 2006; Rosenberg et al., 2006). MiR-206 is generated with miR-133b from a bicistronic transcript from an intergenic region of human chromosome 6. MiR-133b was shown to be decreased in patients with Parkinson's disease and to regulate maturation of dopaminergic neurons (Kim et al., 2007). MiR-1-1 and miR-1-2 are identical to each other and differ from miR-206 by four nucleotides. MiR-133a-1 and miR-133a-2 are identical to each other and differ from miR-133b by two nucleotides The stem-loop and mature sequences for miR-206, miR-1, miR-133a, and miR-133b are shown below:

```
Human miR-206 stem-loop (SEQ ID NO: 1):
UGCUUCCCGAGGCCACAUGCUUCUUUAUAUCCCCAUAUGGAUUACUUUGC

UAUGGAAUGUAAGGAAGUGUGUGGGUUUCGGCAAGUG

Human mature miR-206 (SEQ ID NO: 2):
UGGAAUGUAAGGAAGUGUGUGG

Human miR-1 stem-loop (SEQ ID NO: 3):
ACCUACUCAGAGUACAUACUUCUUUAUGUACCCAUAUGAACAUACAAUGC

UAUGGAAUGUAAAGAAGUAUGUAUUUUUGGUAGGC

Human mature miR-1 (SEQ ID NO: 4):
UGGAAUGUAAAGAAGUAUGUAU

Human miR-133a stem-loop (SEQ ID NO: 5):
ACAAUGCUUUGCUAGAGCUGGUAAAAUGGAACCAAAUCGCCUCUUCAAUG

GAUUUGGUCCCCUUCAACCAGCUGUAGCUAUGCAUUGA

Human mature miR-133a (SEQ ID NO: 6):
UUUGGUCCCCUUCAACCAGCUG

Human miR-133b stem-loop (SEQ ID NO: 7):
CCUCAGAAGAAAGAUGCCCCCUGCUCUGGCUGGUCAAACGGAACCAAGUC

CGUCUUCCUGAGAGGUUUGGUCCCCUUCAACCAGCUACAGCAGGGCUGGC

AAUGCCCAGUCCUUGGAGA

Human mature miR-133b (SEQ ID NO: 8):
UUUGGUCCCCUUCAACCAGCUA
```

In one embodiment, the present invention provides a method of treating a subject afflicted with a denervating neuropathic state comprising administering to the subject an agonist of miR-206 and/or miR-1. An "agonist" can be any compound or molecule that increases the activity or expression of the particular miRNA. For example, in certain embodiments, an agonist of miR-206 and/or miR-1 can be a polynucleotide comprising a mature miR-206 and/or miR-1 sequence. In some embodiments, the polynucleotide comprises the sequence of SEQ ID NO: 2, and/or SEQ ID NO: 4. In another embodiment, the agonist of miR-206 and/or miR-1 can be a polynucleotide comprising the pri-miRNA or pre-miRNA sequence for miR-206 and/or miR-1. In such an embodiment, the polynucleotide can comprise a sequence of SEQ ID NO: 1 and/or SEQ ID NO: 3. The polynucleotide comprising the mature sequence, the pre-miRNA sequence, or the pri-miRNA sequence for miR-206 and/or miR-1 can be single stranded or double stranded. The polynucleotides can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages and combinations comprising the same. In one embodiment, the polynucleotide comprising a miR-206 and/or miR-1 sequence is conjugated to cholesterol.

In another embodiment, the agonist of miR-206 and/or miR-1 can be an agent distinct from miR-206 and/or miR-1 that acts to increase, supplement, or replace the function of miR-206 and/or miR-1. For instance, MyoD and the bHLH protein E12, both of which up-regulate expression of miR-206, can be agonists of miR-206. Other transcription factors or signaling proteins that up-regulate the expression of miR-206 and/or miR-1 are likewise contemplated as agonists of miR-206 and/or miR-1.

In another embodiment, the agonist of miR-206 and/or miR-1 can be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-206 and/or miR-1 comprises a promoter "operably linked" to a polynucleotide encoding miR-206 and/or miR-1. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding miR-206 and/or miR-1 may encode the primary miRNA sequence (pri-miRNA), the precursor-miRNA sequence (pre-miRNA), or the mature miRNA sequence for miR-206 and/or miR-1. In another embodiment, the expression vector comprises a polynucleotide operably linked to a promoter, wherein said polynucleotide comprises the sequence of SEQ ID NO: 1. In another embodiment, the expression vector comprises a polynucleotide operably linked to a promoter, wherein said polynucleotide comprises the sequence of SEQ ID NO: 2. In another embodiment, the expression vector comprises a polynucleotide operably linked to a promoter, wherein said polynucleotide comprises the sequence of SEQ ID NO: 3. In another embodiment, the expression vector comprises a polynucleotide operably linked to a promoter, wherein said polynucleotide comprises the sequence of SEQ ID NO: 4. The polynucleotide comprising the sequence of SEQ ID NO: 1, SEQ ID NO: 2, SEQ ID NO: 3, or SEQ ID NO: 4 may be about 18 to about 2000 nucleotides in length, about 70 to about 200 nucleotides in length, about 20 to about 50 nucleotides in length, or about 18 to about 25 nucleotides in length.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III.

In some embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the polynucleotide sequence of interest. The use of other viral or mammalian cellular or bacterial phage promoters which are well-known in the art to achieve expression of a polynucleotide sequence of interest is contemplated as well, provided that the levels of expression are sufficient for a given purpose. In certain embodiments, a tissue-specific promoter, such as a skeletal muscle-specific promoter, can be used to obtain tissue-specific expression of the polynucleotide sequence of interest.

By employing a promoter with well-known properties, the level and pattern of expression of the protein of interest following transfection or transformation can be optimized. Further, selection of a promoter that is regulated in response to specific physiologic signals can permit inducible expression of the polynucleotide. Tables 1 and 2 list several regulatory elements that may be employed, in the context of the present invention, to regulate the expression of the polynucleotide of interest (e.g. agonists of miR-206 and/or miR-1). This list is not intended to be exhaustive of all the possible elements involved in the promotion of gene expression but, merely, to be exemplary thereof.

Below is a list of viral promoters, cellular promoters/enhancers and inducible promoters/enhancers that could be used in combination with the polynucleotide of interest in an expression construct (Table 1 and Table 2). Additionally, any promoter/enhancer combination (as per the Eukaryotic Promoter Data Base EPDB) could also be used to drive expression of the polynucleotide. Eukaryotic cells can support cytoplasmic transcription from certain bacterial promoters if the appropriate bacterial polymerase is provided, either as part of the delivery complex or as an additional genetic expression construct.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |

TABLE 1-continued

| Promoter and/or Enhancer | |
|---|---|
| Promoter/Enhancer | References |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/ or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase 1 | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |

TABLE 1-continued

Promoter and/or Enhancer

| Promoter/Enhancer | References |
|---|---|
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, which include the myosin light chain-2 promoter (Franz et al., 1994; Kelly et al., 1995), the α-actin promoter (Moss et al., 1996), the troponin 1 promoter (Bhaysar et al., 1996); the $Na^+/Ca^{2+}$ exchanger promoter (Barnes et al., 1997), the dystrophin promoter (Kimura et al., 1997), the α7 integrin promoter (Ziober and Kramer, 1996), and the muscle creatine kinase (MCK) promoter (Jaynes et al., 1988; Horlick et al., 1989; Johnson et al., 1989).

A polyadenylation signal may be included to effect proper polyadenylation of the gene transcript where desired. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed.

However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing agonists of miR-206 and/or miR-1 in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell, the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment.

Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes.

In a particular example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

In one embodiment, the present invention provides a method of treating a subject afflicted with a denervating neuropathic state. A "denervating neuropathic state" refers to a condition in which there is a loss of nerve supply to one or more tissues as a result of a disease or injury. Denervating neuropathic states can result from degenerative motor neuron diseases, such as myasthenia gravis, polio, amyotrophic lateral sclerosis (ALS), Friedreich's ataxia, spinal muscular atrophy, or spinocerebellar ataxia.

In one embodiment, the present invention provides a method of treating a subject suffering from myasthenia gravis by administering to the subject an agonist of miR-206 and/or miR-1. Myasthenia gravis (MG) is a neuromuscular disease leading to fluctuating muscle weakness and fatiguability. It is an autoimmune disorder, in which weakness is caused by circulating antibodies that block acetylcholine receptors at the post-synaptic neuromuscular junction, inhibiting the stimulative effect of the neurotransmitter acetylcholine. Myasthenia is treated medically with cholinesterase inhibitors or immunosuppressants, and, in selected cases, thymectomy. The hallmark of myasthenia gravis is muscle weakness that increases during periods of activity and improves after periods of rest. Muscles that control eye and eyelid movement, facial expression, chewing, talking, and swallowing are especially susceptible. The muscles that control breathing and neck and limb movements can also be affected.

In another embodiment, the present invention includes a method of treating ALS in a subject in need thereof comprising administering to the subject an agonist of miR-206 and/or miR-1. ALS (also called Lou Gehrig's Disease, or Maladie de Charcot) is a progressive, usually fatal, neurodegenerative disease caused by the degeneration of motor neurons. As one of the motor neuron diseases, the disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy due to that denervation. The patient may ultimately lose the ability to initiate and control all voluntary movement except of the eyes. Riluzole, the first FDA-approved treatment for ALS, slows the degeneration of motor neurons, but does not reverse the damage that has already occurred. Other treatments for ALS are designed to relieve symptoms and improve the quality of life for patients.

In another embodiment, the present invention provides a method for treating spinal muscular atrophy in a subject in need thereof by administering an agonist of miR-206 and/or miR-1. Spinal muscular atrophy (SMA) is an autosomal recessive disorder which is the leading hereditary cause of infant death in humans. The disease is characterized by a progressive muscle weakness from proximal to distal with lower limbs more greatly affected than upper limbs. Three types of SMA have been described based on disease severity and age of onset. Type I affects approximately fifty percent of SMA patients with symptoms presenting within the first six months after birth. Death typically occurs within the first two years due to respiratory failure. Type II SMA has an onset between six months and eighteen months of age, and length of survival is dependent on the severity of respiratory impairment. Type III SMA patients, who have symptom onset between eighteen months and early childhood, usually do not have a decrease in life expectancy, although most are wheel chair bound at some point in their disease progression. SMA is characterized by loss of alpha-motor neurons in the anterior horn of the spinal cord, which is correlated with muscle paralysis and atrophy. Currently, there are no effective therapeutics for SMA disease.

In still another embodiment, the present invention provides a method of treating Friedreich's ataxia in a subject in need thereof comprising administering to the subject an agonist of miR-206 and/or miR-1. Friedreich's ataxia is an autosomal recessive congenital disease that causes progressive damage to the nervous system resulting in symptoms ranging from gait disturbance and speech problems to heart disease. The ataxia of Friedreich's ataxia results from the degeneration of nerve tissue in the spinal cord, in particular sensory neurons essential (through connections with the cerebellum) for directing muscle movement of the arms and legs. The spinal cord becomes thinner and nerve cells lose some of their myelin sheath. Symptoms of Friedreich's ataxia include any combination, but not necessarily all of the following: muscle weakness in the arms and legs, loss of coordination, vision impairment, hearing loss, slurred speech, curvature of the spine (scoliosis), high plantar arches, diabetes, and heart disorders (e.g., atrial fibrillation, and resultant tachycardia, and hypertrophic cardiomyopathy). The symptoms can be treated but there is no treatment for Friedrich's Ataxia at this time.

In yet another embodiment, the present invention provides a method of treating spinocerebellar ataxia in a subject in need thereof comprising administering to the subject an agonist of miR-206 and/or miR-1. Spinocerebellar ataxia (SCA) is a genetic disease characterized by slowly progressive incoordination of gait and often associated with poor coordination of hands, speech, and eye movements. Frequently, atrophy of the cerebellum occurs. There is no known cure for spinocerebellar ataxia, which is a progressive disease. As with other forms of ataxia, SCA results in unsteady and clumsy motion of the body due to a failure of the fine coordination of muscle movements, along with other symptoms. A person with this disease will usually end up needing to use a wheelchair, and eventually they may need assistance to perform daily tasks.

Denervating neuropathic states can also result from nerve injury, such as spinal cord or peripheral nerve injury, where one or more nerves are transected or crushed. Traumatic spinal cord injury can be classified into different types. Central Cord syndrome is associated with greater loss of upper limb function compared to lower limbs. The Brown-Séquard syndrome results from injury to one side with the spinal cord, causing weakness and loss of proprioception on the side of the injury and loss of pain and thermal sensation of the other side. The Anterior Spinal syndrome results from injury to the anterior part of the spinal cord, causing weakness and loss of pain and thermal sensations below the injury site but preservation of proprioception that is usually carried in the posterior part of the spinal cord. Tabes Dorsalis results from injury to the posterior part of the spinal cord, usually from infection diseases such as syphilis, causing loss of touch and proprioceptive sensation. Conus Medullaris syndrome results from injury to the tip of the spinal cord, located at L1 vertebra. Cauda Equina syndrome is an injury to the spinal roots below the L1 vertebra. Traumatic spinal cord injury and other types of nerve injury can be treated by agonists of miR-206 and/or miR-1, which promote reinervation of skeletal muscle following injury.

In another embodiment of the invention, it is envisioned to use an agonist of miR-206 and/or miR-1 in combination with other therapeutic modalities. Thus, in addition to the miRNA agonists of the invention described herein, one may also provide to the subject "standard" pharmaceutical therapies. Such standard therapies will depend upon the particular denervating neuropathic state to be treated, but can include Riluzole, cholinesterase inhibitors (e.g. edrophonium chloride (Tensilon®, Reversol®), neostigmine, pyridostigmine, physostigmine, ambenonium, demarcarium, rivastigmine, phenanthrene derivatives, galantamine, piperidines, donepezil, and tacrine) and immunosuppressants (e.g. prednisone, cyclosporine, mycophenolate mofetil and azathioprine).

Combinations may be achieved by contacting skeletal muscle cells with a single composition or pharmacological formulation that includes both agents, or by contacting the cell with two distinct compositions or formulations, at the same time, wherein one composition includes an agonist of miR-206 and/or miR-1 and the other includes the second agent. Alternatively, the therapy using an miRNA agonist may precede or follow administration of the other agent(s) by intervals ranging from minutes to weeks. In embodiments where the other agent and miRNA agonists are applied separately to the cell, one would generally ensure that a significant period of time did not expire between the time of each delivery, such that the agent and miRNA agonists would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a miRNA agonist, or the other agent will be desired. In this regard, various combinations may be employed. By way of illustration, where the miRNA agonist is "A" and the other agent/therapy is "B," the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated.

The present invention also contemplates methods for scavenging or clearing miR-206 and/or miR-1 agonists following treatment. In one embodiment, the method comprises overexpression of binding site regions for miR-206 and/or miR-1 in skeletal muscle cells using a muscle specific promoter. The binding site regions preferably contain a sequence of the seed region, the 5' portion of a miRNA spanning bases 2-8, for miR-206 and/or miR-1. In some embodiments, the binding site may contain a sequence from the 3' UTR of one or more targets of miR-206 and/or miR-1. For instance, in one embodiment, a binding site for miR-206 and/or miR-1 contains the 3' UTR of HDAC4. In another embodiment, a miR-206 and/or miR-1 inhibitor may be administered after a miR-206 and/or miR-1 agonist to attenuate or stop the function of the microRNA. Such inhibitors can include antagomirs, antisense, or inhibitory RNA molecules (e.g. siRNA or shRNA).

The present invention also encompasses pharmaceutical compositions comprising an agonist of miR-206 and/or miR-1 and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, can be used as delivery vehicles for the agonists of microRNA function described herein. Commercially available fat emulsions that are suitable for delivering the nucleic acids of the invention to tissues, such as skeletal muscle tissue, include Intralipid®, Liposyn®, Liposyn® II, Liposyne® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO 03/093449, which are herein incorporated by reference in their entireties.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the nucleic acids of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, transdermal, subcutaneous, intramuscular, intraperitoneal or intravenous injection, or by direct injection into skeletal muscle tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Pharmacological therapeutic agents and methods of administration, dosages, etc., are well known to those of skill in the art (see for example, the "Physicians Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Suitable dosages include about 20 mg/kg to about 200 mg/kg, about 40 mg/kg to about 160 mg/kg, or about 80 mg/kg to about 100 mg/kg. Some variation in dosage will necessarily occur depending on the condition of the subject being treated. The person responsible for administration will, in any event, determine the appropriate dose for the individual subject, and such individual determinations are within the skill of those of ordinary skill in the art. Moreover, for human administration, preparations should meet sterility, pyrogenicity, general safety and purity standards as required by FDA Office of Biologics standards.

Any of the compositions described herein may be comprised in a kit. In a non-limiting example, a miR-206 and/or miR-1 agonist is included in a kit. The kit may further include water and hybridization buffer to facilitate hybridization of the two strands of the miRNAs. The kit may also include one or more transfection reagent(s) to facilitate delivery of the polynucleotide agonists to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the miRNAs/polynucleotides or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA agonist by various administration routes, such as parenteral or intramuscular administration.

The present invention also includes a method for diagnosing a denervating neuropathic state in a subject. In one embodiment, the method comprises (a) obtaining a skeletal muscle tissue sample from the subject; (b) assessing activity or expression of miR-206 and/or miR-133b in said sample; and (c) comparing the activity or expression in step (b) with the activity or expression of miR-206 and/or miR-133b in a normal tissue sample, wherein an increase in the activity or expression of miR-206 and/or miR-133b as compared to the activity or expression of miR-206 and/or miR-133b in a normal tissue sample is diagnostic of a denervating neuropathic state. In another embodiment, the method comprises (a) obtaining a skeletal muscle tissue sample from the subject; (b) assessing activity or expression of miR-1 and/or miR-133a in said sample; and (c) comparing the activity or expression in step (b) with the activity or expression of miR-1 and/or miR-133a in a normal tissue sample, wherein a decrease in the activity or expression of miR-1 and/or miR-133a as compared to the activity or expression of miR-1 and/or miR-133a in a normal tissue sample is diagnostic of a denervating neuropathic state. The denervating neuropathic state can include spinal cord injury, myasthenia gravis, amyotrophic lateral sclerosis, Friedreich's ataxia, spinal muscular atrophy, and spinocerebellar ataxia.

In one embodiment, assessing miR-206 and/or miR-133b activity comprises assessing the activity of one or more genes regulated by miR-206 and/or miR-133b. For instance, in some embodiments, the one or more genes regulated by miR-206 is HDAC4, Dach2, or myogenin. In another embodiment, assessing miR-1 and/or miR-133a activity comprises assessing the activity of one or more genes regulated by miR-1 and/or miR-133a. In another embodiment, the method further comprises administering to the subject a therapy for said denervating neuropathic state and reassessing miR-206/miR-133b and/or miR-1/miR-133a expression or activity. The expression or activity of miR-206/miR-133b and/or miR-1/miR-133a obtained following treatment can be compared to expression of these miRNAs in a normal tissue sample or a tissue sample obtained from the subject previously (e.g. prior to treatment).

The present invention further comprises methods for identifying modulators of neuromuscular synapse maintenance and regeneration. For instance, in one embodiment, the present invention provides a method for identifying a modulator of miR-206 and/or miR-1 activity in skeletal muscle. Identified agonists of the function of miR-206 and/or miR-1 are useful in the treatment of denervating neuropathic states, such as ALS or nerve injury. Modulators (e.g. agonists) of miR-206 and/or miR-1 can be included in pharmaceutical compositions for the treatment of denervating neuropathic states according to the methods of the present invention.

These assays may comprise random screening of large libraries of candidate substances; alternatively, the assays may be used to focus on particular classes of compounds selected with an eye towards structural attributes that are believed to make them more likely to inhibit the expression and/or function of miR-206 and/or miR-1.

To identify a modulator of miR-206 and/or miR-1, one generally will determine the function of miR-206 and/or miR-1 in the presence and absence of the candidate compound, optionally in the context of a neuromuscular synapse maintenance and regeneration cell or animal model. For example, a method generally comprises: (a) contacting a skeletal muscle cell with a candidate compound; (b) assessing miR-206 and/or miR-1 activity or expression; and (c) comparing the activity or expression in step (b) with the activity or expression in the absence of the candidate compound, wherein a difference between the measured activities or expression indicates that the candidate compound is a modulator of miR-206 and/or miR-1, and hence neuromuscular synapse maintenance and regeneration. Assays also may be conducted in isolated cells, organs, or in living organisms.

Assessing the activity or expression of miR-206 and/or miR-1 can comprise assessing the expression level of miR-206 and/or miR-1. Those in the art will be familiar with a variety of methods for assessing RNA expression levels including, for example, northern blotting or RT-PCR. Assessing the activity or expression of miR-206 and/or miR-1 can comprise assessing the activity of miR-206 and/or miR-1. In some embodiments, assessing the activity of miR-206 and/or miR-1 comprises assessing neuromuscular junction stability. In other embodiments, assessing the activity of miR-206 and/or miR-1 comprises assessing expression or activity of a gene regulated by miR-206 and/or miR-1. Genes regulated by miR-206 and/or miR-1 include, for example, HDAC4, Dach2, and myogenin. Those in the art will be familiar with a variety of methods for assessing the activity or expression of genes regulated by miR-206 and/or miR-1. Such methods include, for example, northern blotting, RT-PCR, ELISA, or western blotting.

It will, of course, be understood that all the screening methods of the present invention are useful in themselves notwithstanding the fact that effective candidates may not be found. The invention provides methods for screening for such candidates, not solely methods of finding them.

As used herein the term "candidate compound" refers to any molecule that may potentially modulate the neuromuscular synapse maintenance and regeneration function of miR-206 and/or miR-1. One will typically acquire, from various commercial sources, molecular libraries that are believed to meet the basic criteria for useful drugs in an effort to "brute force" the identification of useful compounds. Screening of such libraries, including combinatorially-generated libraries, is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds. Non-limiting examples of candidate compounds that may be screened according to the methods of the present invention are proteins, peptides, polypeptides, polynucleotides, oligonucleotides or small molecules. Modulators of miR-206 and/or miR-1 may also be agonists or inhibitors of upstream regulators of miR-206 and/or miR-1.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads. For example, one may assess the hybridization of an oligonucleotide to a target miRNA.

A technique for high throughput screening of compounds is described in WO 84/03564. Large numbers of small compounds may be synthesized on a solid substrate, such as plastic pins or some other surface. Such molecules can be rapidly screened for their ability to hybridize to miR-206 and/or miR-1.

The present invention also contemplates the screening of compounds for their ability to modulate miR-206 and/or miR-1 expression and function in cells. Various cell lines, including those derived from skeletal muscle cells (e.g. C2C12 cells), can be utilized for such screening assays, including cells specifically engineered for this purpose.

In vivo assays involve the use of various animal models of neuromuscular synapse maintenance and regeneration (e.g. G93A-SOD1 transgenic mice). Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal derived from any of these species, including those modified to provide a model of neuromuscular synapse maintenance and regeneration.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of synapse architecture or signaling. Also, measuring toxicity and dose response can be performed in animals in a more meaningful fashion than in in vitro or in cyto assays.

The present invention includes a method of regulating expression of HDAC4 in a cell comprising contacting the cell with a modulator of a miR-206 and/or miR-1. In one embodiment, the expression of HDAC4 is decreased in the cell following administration of a miR-206 and/or miR-1 agonist. In another embodiment, the expression of HDAC4 is increased in the cell following administration of a miR-206 and/or miR-1 inhibitor. In certain embodiments, the cell is a skeletal muscle cell.

In another embodiment, the present invention provides a method of attenuating or eliminating the expression or activity of miR-206 in a cell by delivering to the cell an inhibitor of miR-206. The cell may be in vitro or in vivo. Inhibitors of miR-206 can include antisense oligonucleotides, antagomirs, and inhibitory RNA molecules (e.g. shRNA and siRNA). Antisense oligonucleotides may comprise a sequence that is at least partially complementary to a mature miR-206 sequence, e.g. at least about 75%, 80%, 85%, 90%, 95%, 96%, 97%, 98%, or 99% complementary to a mature miR-206 sequence. In some embodiments, the antisense oligonucleotide may be substantially complementary to a mature miR-206 sequence, that is at least about 95%, 96%, 97%, 98%, or 99% complementary to a target polynucleotide sequence. In one embodiment, the antisense oligonucleotide comprises a sequence that is 100% complementary to a mature miR-206 sequence. In some embodiments, the antisense oligonucleotides are antagomirs. "Antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol or other moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miR-206 sequence. In some embodiments, the antagomir may be substantially complementary to a mature miR-206 sequence, that is at least about 95%, 96%, 97%, 98%, or 99% complementary to a target polynucleotide sequence. In other embodiments, the antagomirs are 100% complementary to the mature miR-206 sequence.

Another approach for inhibiting the function of miR-206 is administering an inhibitory RNA molecule having a double stranded region that is at least partially identical and partially complementary to a mature sequence of miR-206. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical and partially complementary, e.g. about 75%, 80%, 85%, 90%, 95%, 96%, 97%, 98%, or 99% identical and complementary, to the mature miR-206 sequence. In some embodiments, the double-stranded regions of the inhibitory RNA comprise a sequence that is at least substantially identical and substantially complementary to the mature miR-206 sequence. "Substantially identical and substantially complementary" refers to a sequence that is at least about 95%, 96%, 97%, 98%, or 99% identical and complementary to a target polynucleotide sequence. In other embodiments, the double-stranded regions of the inhibitory RNA molecule may contain 100% identity and complementarity to the miR-206 sequence.

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Figure 1:
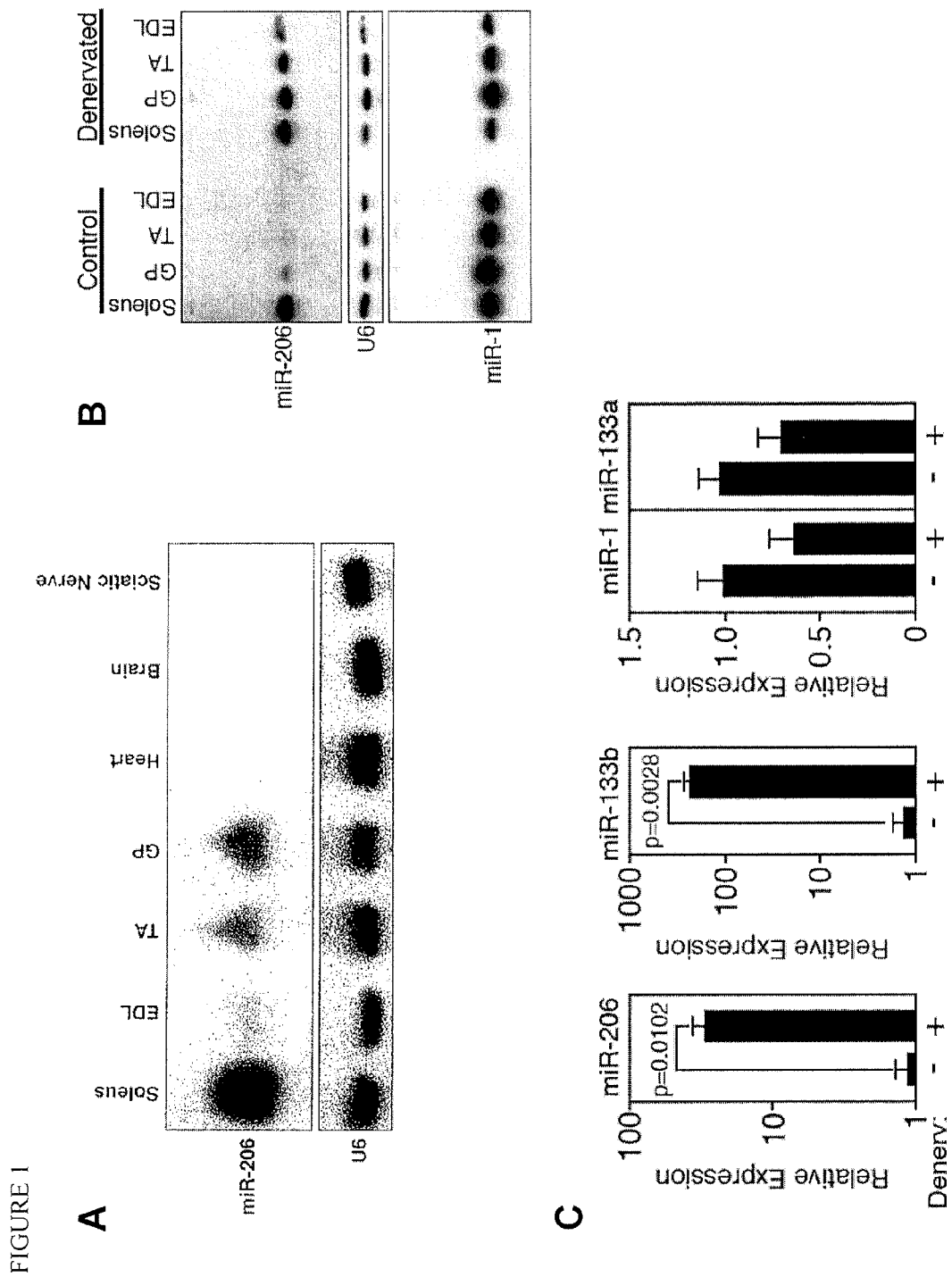
FIG. 1. Upregulation of miR-206 in Denervated Muscle.

The Slow Skeletal Muscle-Enriched miR-206 is Upregulated in Denervated Skeletal Muscle MiR-206 is a muscle-specific miRNA that is closely related in sequence to miR-1 and shares the same seed region. In contrast to miR-1, which is expressed in the heart and skeletal muscle, miR-206 is expressed solely in skeletal muscle. Northern blot analysis of different skeletal muscles revealed that miR-206 is highly enriched in muscle groups that contain slow fibers such as the soleus (FIG. 1A). MiR-1 is expressed at similar levels in all muscle groups (FIG. 1B).

MiRNA expression profiles of skeletal muscles from the lower limbs of normal adult mice and mice subjected to surgical resection of the sciatic nerve for 10 days were compared. Of 320 miRNAs tested, levels of 16 miRNAs were significantly affected (up or downregulated>2-fold) in response to denervation. MiR-206 was one of the most dramatically upregulated miRNAs in denervated muscle. Northern blot (FIG. 1B) and real time PCR (FIG. 1C) confirmed that miR-206 was upregulated following denervation. Upregulation was dramatic in three muscles that contain predominantly fast-twitch fibers, extensor digitorum longus (EDL), tibialis anterior (TA) and gastrocnemius/plantaris (G/P) (FIG. 1B). MiR-206 levels were higher in normally innervated soleus, which contains predominantly slow myofibers, and upregulation following denervation was correspondingly less striking. Consistent with its transcription from the same promoter as miR-206, miR-133b was also upregulated following denervation, whereas miR-1 and miR-133a were downregulated approximately 50 percent in response to denervation (FIGS. 1B and 1C). These results indicate that miR-206 may play a role in muscle repair after nerve injury. In addition, the data suggest that although miR-206 and miR-1 are similar in sequence, the expression pattern and differential response to various stimuli suggest unique functions for these two miRNAs.

Example 2

Delayed Re-Innervation of Skeletal Muscle in mIR-206 Knockout Mice after Nerve Injury To determine the in vivo function of miR-206, miR-206 knockout mice were generated. MiR-206 is transcribed as a bicistronic pre-miRNA with miR-133b. The targeting strategy was designed to abolish the expression of miR-206 and retain the expression of miR-133b (FIGS. 2A and B). The 2.7-kb 5' arm was amplified from 129SvEv genomic DNA and digested with Sac II and Not I and ligated into pGKNeo-F2L2DTA targeting vector. The 2.1-kb 3' arm was digested with Hind III and Eco RV and ligated between the neomycin resistance and DTA cassettes of the targeting vector. Targeted ES-cells were identified by Southern blotting with 5' and 3' external probes. One clone with a properly targeted miR-206 allele was used for injection into 3.5 day C57BL/6 blastocysts and the resulting chimeras were bred to C57BL/6 females for germline transmission.

Southern blot of genomic DNA from wild-type and miR-206 heterozygotes confirmed correct targeting and germline transmission of the mutant allele (FIG. 2C). The absence of mature miR-206 in the skeletal muscle of mutant mice was confirmed by Northern blot analysis (FIG. 2D). Deletion of miR-206 had no effect on expression of linked pre-miR-133b or the closely related miR-1-2 or miR-1-2 (FIG. 2E). Mice homozygous for the targeted deletion of miR-206 were viable and showed no gross abnormalities in weight, behavior, or the overall architecture or fiber-type distribution of skeletal muscle as seen by H&E and metachromatic ATPase staining (FIG. 2F).

A transcript derived from the miR-206/133b locus was originally identified as a synapse-associated non-coding RNA (referred to as 7H4) by Merlie and colleagues (Velleca et al., 1994). Presumably 7H4 is selectively transcribed by myonuclei associated with the neuromuscular junction (NMJ), as has been shown for genes encoding neurotransmitter receptor genes and other components of the postsynaptic apparatus (Sanes et al., 1991; Sunesen and Changeux, 2003). Although the reported 7H4 sequence did not include miR-206, RT-PCR demonstrated that miR-206 sequences are included in this transcript and confirmed that miR-206, like 7H4, is enriched in synaptic regions of muscle fibers (data not shown). Therefore, the original 7H4 RNA (Velleca et al., 1994) appears to represent a partially processed pri-miRNA from the miR-206/133b locus. These results, along with the lack of any obvious phenotype in muscle structure or function, focused our attention on the NMJ. The architecture of NMJs in the TA, EDL, and soleus muscles of neonatal and adult wild-type and miR-206–/– mice was examined. The post-synaptic membrane was visualized using fluorescently-tagged Bungarotoxin (BTX), which binds to acetylcholine receptors (AChRs). The motor axon and the nerve terminal were detected with antibodies to neurofilament proteins and antibodies to the synaptic vesicle protein, synaptotagmin 2 (ZNP) (Fox et al., 2007), respectively. The NMJs of neonatal and adult mutant mice showed no obvious differences when compared to age-matched wild-type NMJs (data not shown). Thus, miR-206 is dispensable for formation and maturation of the NMJ.

Figure 3C:
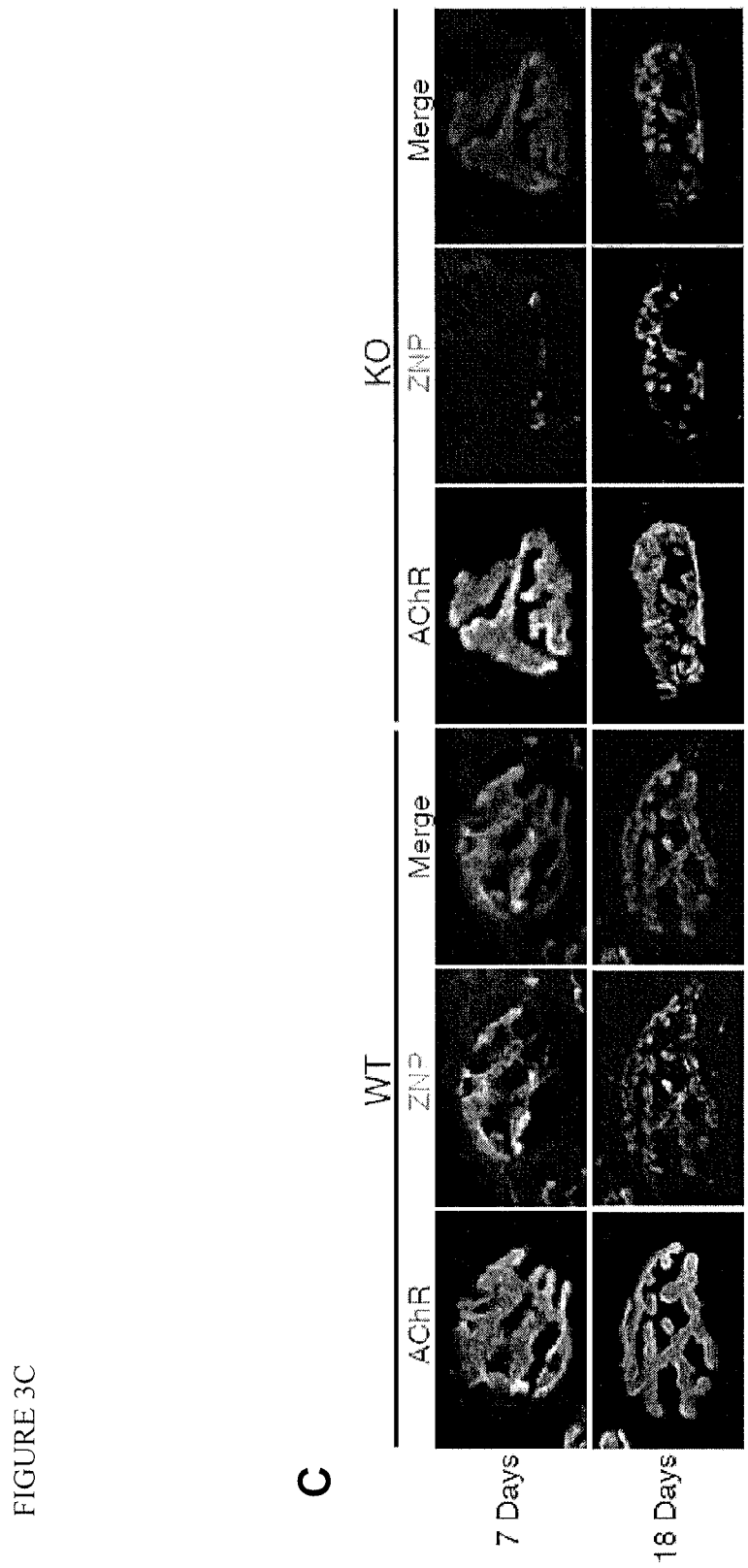

Given the robust upregulation of miR-206 in denervated muscle, we next asked whether miR-206 might regulate reinnervation following nerve injury. The sciatic nerve of miR-206–/– and control wild-type littermates was cut in the midthigh and reinnervation of the TA muscle was assessed 1-8 weeks later. Regenerating axons preferentially reinnervate original synaptic sites following denervation (Sanes and Lichtman, 1999), so the number of postsynaptic sites apposed by nerve was quantified. Because the post-synaptic AChRs remain largely intact following denervation, reinnervation can be accurately assessed by the superimposition of BTX staining (red) with ZNP staining (green). In wild-type mice, reinnervation began between 2 and 3 weeks after denervation, and was nearly complete by 5 weeks post-injury (FIGS. 3A and B). In contrast, reinnervation of miR-206–/– TA muscles did not begin until 3 weeks post-injury, and remained retarded at 5 weeks-post injury (FIGS. 3A and B). Reinnervation was also delayed when the nerve was crushed rather than cut; in this procedure, no gap in the nerve is generated and regeneration to targets occurs more rapidly than after nerve cut (FIG. 3C). Similar results were obtained in the gastrocnemius and EDL muscles (data not shown). Thus, in several muscles and following two types of nerve injury, reinnervation was significantly delayed in the absence of miR-206, suggesting that miR-206 has an essential role in regulating re-innervation of neuromuscular junctions following injury.

Successful reinnervation following nerve transection involves a series of steps. First, a growth program is triggered in axotomized neurons and their axons regenerate through the distal stump to reach the muscle. As expected, these steps were unaffected in the mutant animals as a similar number of nerve fibers were observed in wild-type and miR-206–/– nerves, even though few NMJs had yet formed in the mutant muscle (data not shown). These results indicate that axonal regeneration per se was unimpaired in the miR-206 knockout animals.

Another set of steps occurs intramuscularly when axons branch, contact and re-occupy muscle fibers, and finally form new nerve terminals specialized for neurotransmitter release. The prolonged delay in reinnervation in the absence of miR-206 suggests that miR-206 regulates a signal emanating from muscle that influences interaction of the motor nerve with the NMJ following injury. Consistent with this conclusion, reinnervation of original synaptic sites on miR-206–/– muscle fibers was aberrant in multiple ways. First, many synaptic sites were only partially re-occupied by the regenerated nerve in the mutant mice. Second, levels of synaptotagmin 2 (ZNP) were lower in the terminal regions of miR-206–/– than in control mice. Conversely, in preterminal regions of motor axons, levels of synaptotagmin 2 were higher in mutants than in controls. Thus, the vesicles fail to aggregate properly in regenerated nerve terminals of mutants. Finally, motor axons often sprouted beyond miR-206–/– NMJs, suggesting a possible lack of "stop" signals emanating from the muscle (data not shown).

Example 3

MiR-206 Targets HDAC4 in Skeletal Muscles

Among the many computationally predicted targets of miR-206, histone deacetylase 4 (HDAC4) mRNA is among the strongest. The 3' UTR of the mouse Hdac4 mRNA contains two evolutionarily conserved sequences with perfect complementarity to the seed sequence of miR-206 (FIG. 4A). Moreover, HDAC4 has been implicated in the control of neuromuscular gene expression (Cohen et al., 2005, Tang et al., 2008). Also, the closely related miRNA, miR-1, has been shown to inhibit translation of HDAC4 mRNA in vitro (Chen et al., 2006). To test if miR-206 was capable of repressing HDAC4 translation, the 3' UTR of HDAC4 mRNA was cloned downstream of a luciferase reporter under control of the CMV promoter. Transfection of increasing amounts of miR-206 resulted in a dose-dependent decrease in luciferase activity, and mutation of the miR-206 target sequences in the HDAC4 3'UTR prevented repression by miR-206 (FIG. 4B). HDAC4 protein expression was increased in skeletal muscle of miR-206–/– animals compared to wild-type controls (FIG. 4C). Hdac4 mRNA levels were not changed in miR-206–/– mice, indicating that miR-206 acts in this instance by translational inhibition rather than by mRNA destabilization (Valencia-Sanchez et al., 2006) (FIG. 4D). Previous work has demonstrated that HDAC4 induces myogenin expression through the repression of Dach2 expression, a repressor of myogenin (Cohen et al., 2007, Tang et al., 2009). As expected, Dach2 transcripts were decreased and myogenin transcripts were increased following denervation in miR-206–/– mice, consistent with increased HDAC4 protein expression and enhanced repression of signaling downstream of HDAC4 in denervated miR-206–/– mice (FIGS. 4E and F).

To test whether HDAC4 mediates effects of miR-206 in muscle, mice with a conditional Hdac4 null allele in which loxP sites flanked exon 6 of the Hdac4 gene were generated, and the allele in skeletal muscle was deleted using transgenic mice that express Cre recombinase specifically in this tissue (HDAC4 mKO) (Potthoff et al., 2007, Li et al., 2005). NMJs formed and matured normally in the absence of HDAC4 (data not shown). However, muscles of HDAC4 mutant mice were reinnervated more rapidly than those of controls following nerve crush or cut (FIG. 4G), a phenotype opposite that of miR-206–/– mice. Likewise, synaptic sites were better covered by regenerating nerve terminals in HDAC4 mutants than in controls, whereas deletion of miR-206 hampered complete occupancy of synaptic sites. These findings are consistent with the conclusion that miR-206 functions to counter-act the negative influence of HDAC4 on reinnervation following injury.

Example 4

Upregulation of mIR-206 in a Mouse Model of Amyotrophic Lateral Sclerosis

In an effort to identify miRNAs that are involved in the pathological progression of amyotrophic lateral sclerosis (ALS), a disease which results in denervation of muscles, a miRNA array profiling of GP muscles of G93A-SOD1 transgenic mice, a recognized mouse model of ALS (Son et al., 2007), was performed. Hemizygous G93A-SOD1 transgenic mice develop progressive neuromuscular deficits by six months, displaying paralysis in one or more limbs soon thereafter and death by nine months (Puttaparthi et al., 2002). The array was performed on the muscles of 7 month-old G93A-

SOD1 transgenic and wild-type mice. Among the many miRNAs that were up and down-regulated in the GP muscles of the G93A-SOD1 mice, miR-206 was found to be the most upregulated (FIG. 5A). Northern blot analysis confirmed the array results and quantification of the bands revealed an approximate 9-fold increase in miR-206 expression and 2-fold decrease in miR-1 expression in the end-stage ALS mice (FIG. 5B and data not shown). Treatment of C2C12 muscle cells with Riluzole, a therapeutic drug used to slow the progression of ALS (McGeer and McGeer, 2005), decreased the expression of miR-206 and increased the expression of miR-1 (data not shown).

Figure 5D:
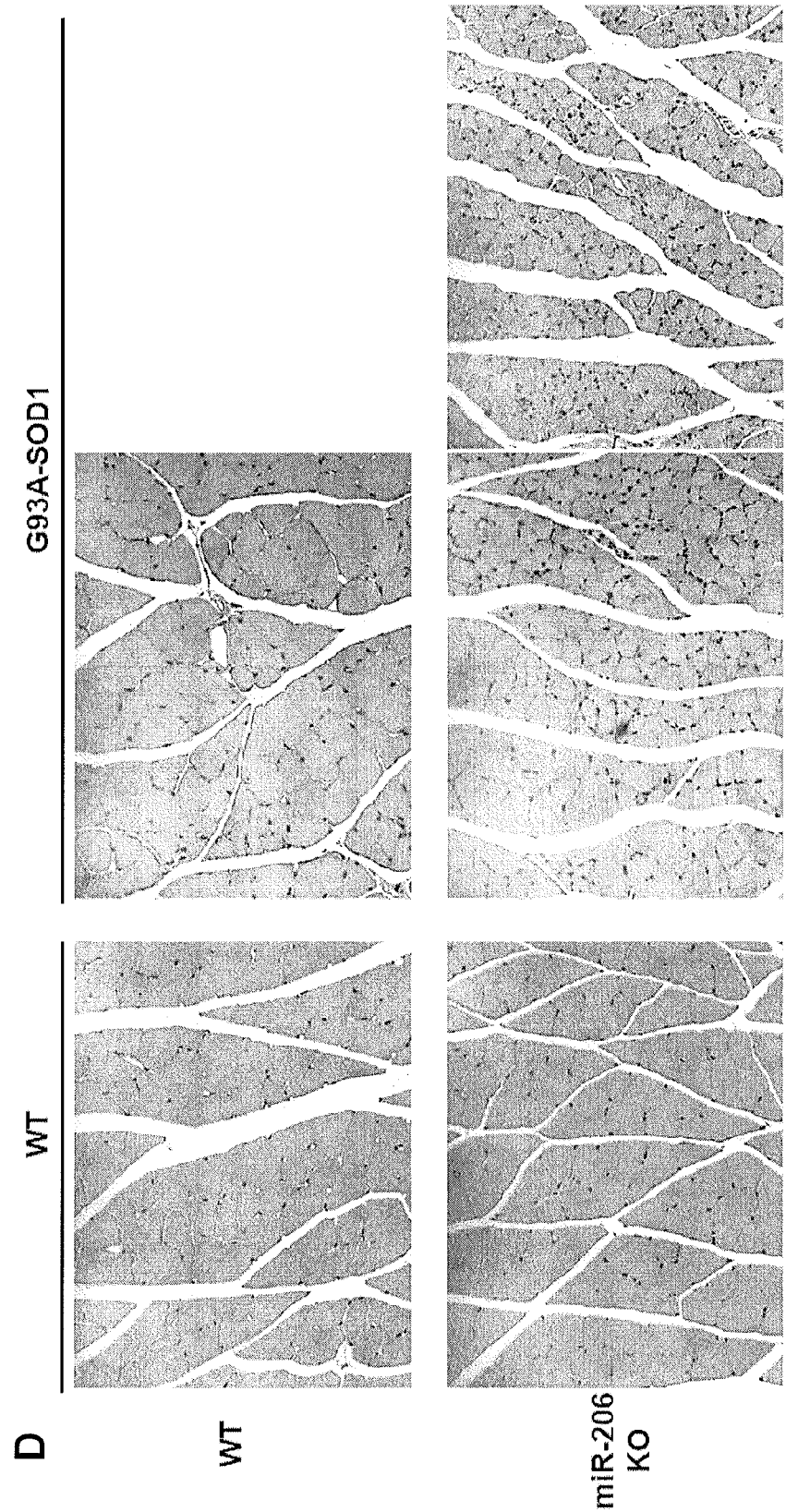

To further elucidate the role of miR-206 in muscle degeneration, double mutant mice were generated by crossing miR-206 mutant animals with G93A-SOD1 animals. ALS pathogenesis was increased in the miR-206/G93A-SOD1 double mutant mice. FIG. 5C depicts a representative image of a G93A-SOD1 mouse and a miR-206/G93A-SOD1 double mutant mouse. Note the enhanced paralysis of the hind limbs in the double mutant mouse. Muscle degeneration was also increased in miR-206/G93A-SOD1 double mutant mice as evidenced by hematoxylin and eosin (H&E) staining of gastrocnemius/plantaris muscles of wild-type, miR-206 knockouts, G93A-SOD1 animals, and miR-206/G93A-SOD1 double mutant mice (FIG. 5D). These results indicate that loss of miR-206 exacerbates neuromuscular degeneration, suggesting that manipulation of miR-206 expression may be a viable therapeutic approach to the treatment of neurodegenerative disorders, such as ALS.

Dysregulation of protein-coding genes in mouse models and patients with ALS has been well described (Boillee et al., 2006; Gonzalez de Aguilar et al., 2007). However, to date the expression profile of miRNAs in ALS has not been reported. We found that the expression of several miRNAs, most notably miR-1 and miR-206, is significantly changed in the muscles of G93A-SOD1 transgenic mice, a recognized mouse model for ALS. Although there appears to be a requirement for damage to motor neurons to initiate the ALS phenotype, other cell types are clearly involved in the pathological progression of the disease (Boillee et al., 2006b). These observations support a role for non-neuronal mRNAs; as well as, miRNAs in impacting the pathological gene networks seen in ALS.

Several mechanisms have been proposed to contribute to the progression of ALS, including oxidative damage, glutamate excitotoxicity, and axonal retrograde transport defects (Dunckley et al., 2007). Our findings demonstrate that a change in the expression of miRNAs is also a likely mechanism contributing to the progression of ALS. While the exact molecular mechanisms that result in motor neuron degeneration in ALS remain vague, it is clear that a common convergence and an initial pathological hallmark of the disease is the denervation of target muscle. Therefore, successful therapeutics should target these early steps in the progression of the disease. The robust increase in the expression of miR-206 in denervated muscle, as well as in G93ASOD1 mice suggests that manipulation of the expression of miR-206 represents a novel potential therapeutic target to treat the clinical symptoms associated with ALS and other motor neuron diseases with dysfunction of the neuromuscular junction.

All publications, patents, and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The use of the word "a" or "an" when used in conjunction with the term "comprising" in the claims and/or the specification may mean "one," but it is also consistent with the meaning of "one or more," "at least one," and "one or more than one." It is contemplated that any embodiment discussed herein can be implemented with respect to any method or composition of the invention, and vice versa. Furthermore, compositions and kits of the invention can be used to achieve methods of the invention. Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

REFERENCES

The following references, to the extent that they provide exemplary procedural or other details supplementary to those set forth herein, are specifically incorporated herein by reference.

U.S. Pat. No. 4,873,191
U.S. Pat. No. 5,604,251
U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Patent Publn. 20020150626
U.S. Patent Publn. 20030032615
U.S. Patent Publn. 20030203865
U.S. Patent Publn. 20040048787
Abraham et al., *Mol. Med*, 8:750-760, 2002.
Ambros, *Cell*, 113(6):673-676, 2003.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Babak et al., *RNA* 10:1813-1819, 2004.
Baichwal and Sugden, *In: Gene Transfer*, Kucherlapati (Ed.), Plenum Press, NY, 117-148, 1986.
Baldwin and Haddad, *J. Appl. Physiol.*, 90:345-357, 2001.
Banerji et al., *Cell*, 27(2 Pt 1):299-308, 1981.

Banerji et al., *Cell,* 33(3):729-740, 1983.
Barad et al., *Genome Res.* 14:2486-2494, 1997.
Barnes et al., *J Biol. Chem.,* 272(17):11510-11517, 1997.
Bartel, *Cell,* 116:281-297, 2004.
Benvenisty and Neshif, *Proc. Natl. Acad. Sci. USA,* 83(24): 9551-9555, 1986.
Berkhout et al., *Cell,* 59:273-282, 1989.
Bhaysar et al., *Genomics,* 35(1):11-23, 1996.
Blanar et al., *EMBO J,* 8:1139, 1989.
Bodine and Ley, *EMBO J,* 6:2997, 1987.
Boshart et al., *Cell,* 41:521, 1985.
Bosze et al., *EMBO J,* 5(7):1615-1623, 1986.
Braddock et al., *Cell,* 58:269, 1989.
Brennecke et al., *Cell,* 113:25-36, 2003.
Brinster et al., *Proc. Natl. Acad. Sci. USA,* 82(13):4438-4442, 1985.
Bristow, *Cardiology,* 92:3-6, 1999.
Bulla and Siddiqui, *J. Virol.,* 62:1437, 1986.
Calin et al., *Proc. Natl. Acd. Sci. USA,* 99:15524-15529, 2002.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Carrington et al. *Science,* 301(5631):336-338, 2003.
Celander and Haseltine, *J Virology,* 61:269, 1987.
Celander et al., *J Virology,* 62:1314, 1988.
Chandler et al., *Cell,* 33:489, 1983.
Chang and Karin, *Nature,* 410(6824):37-40, 2001.
Chang et al., *Biochim. Biophys. Acta,* 1092(2):153-160, 1991.
Chang et al., *Mol. Cell. Biol.,* 9:2153, 1989.
Chang et al., *Nature,* 430(7001):785-789, 2004.
Chatterjee et al., *Proc. Natl. Acad. Sci.* 86:9114, 1989.
Chen and Okayama, *Mol. Cell. Biol.,* 7(8):2745-2752, 1987.
Chen et al., *Mol. Cell. Endocrinol.,* 162:45-55, 2000.
Chen et al., *Science,* 303(5654):83-86, 2004.
Choi et al., *Cell,* 53:519, 1988.
Coffin, In: *Virology,* Fields et al. (Eds.), Raven Press, NY, 1437-1500, 1990.
Cohen et al., *J Cell. Physiol.,* 5:75, 1987.
Costa et al., *Mol. Cell. Biol.,* 8:81, 1988.
Couch et al., *Am. Rev. Resp. Dis.,* 88:394-403, 1963.
Coupar et al., *Gene,* 68:1-10, 1988.
Cripe et al., *EMBO J,* 6:3745, 1987.
Culotta and Harner, *Mol. Cell. Biol.,* 9:1376, 1989.
Dandolo et al., *J Virology,* 47:55-64, 1983.
De Villiers et al., *Nature,* 312(5991):242-246, 1984.
Deschamps et al., *Science,* 230: 1174-1177, 1985.
Dubensky et al., *Proc. Natl. Acad. Sci. USA,* 81:7529-7533, 1984.
Durand et al., *Ann. Med.,* 27:311-317, 1995.
Edbrooke et al., *Mol. Cell. Biol.,* 9:1908, 1989.
Edgerton and Roy, *J Appl. Physiol.,* 89:1224-1231, 2000.
Edlund et al., *Science,* 230:912-916, 1985.
Eichhorn and Bristow, *Circulation,* 94:2285-2296, 1996.
EPO 0273085
Fechheimer, et al., *Proc Natl. Acad. Sci. USA,* 84:8463-8467, 1987.
Feng and Holland, *Nature,* 334:6178, 1988.
Ferkol et al., *FASEB* 7:1081-1091, 1993.
Firak and Subramanian, *Mol. Cell. Biol.,* 6:3667, 1986.
Fitts et al., *J Appl. Physiol.,* 89:823-839, 2000.
Foecking and Hofstetter, *Gene,* 45(1):101-105, 1986.
Fraley et al., *Proc. Natl. Acad. Sci. USA,* 76:3348-3352, 1979.
Franz et al., *Cardioscience,* 5(4):235-43, 1994.
Friedman et al., *Genes Devel.,* 3:1314, 1989.
Fujita et al., *Cell,* 49:357, 1987.
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Ghosh-Choudhury et al., *EMBO J,* 6:1733-1739, 1987.
Gilles et al., *Cell,* 33:717, 1983.
Gloss et al., *EMBO J.,* 6:3735, 1987.
Godbout et al. *Mol. Cell. Biol.,* 8:1169, 1988.
Gomez-Foix et al., *J Biol. Chem.,* 267:25129-25134, 1992.
Goodbourn and Maniatis, *Proc. Natl. Acad. Sci. USA,* 85:1447, 1988.
Goodbourn et al., *Cell,* 45:601, 1986.
Gopal, *Mol. Cell. Biol.,* 5:1188-1190, 1985.
Gopal-Srivastava et al., *J Mol. Cell. Biol.* 15(12):7081-7090, 1995.
Graham and Prevec, In: *Methods in Molecular Biology: Gene Transfer and Expression Protocol,* Murray (Ed.), Humana Press, Clifton, N.J., 7:109-128, 1991.
Graham and Van Der Eb, *Virology,* 52:456-467, 1973.
Graham et al., *J Gen. Virl.,* 36(1):59-74, 1977.
Greene et al., *Immunology Today,* 10:272, 1989
Grishok et al., *Cell,* 106:23-34, 2001.
Grosschedl and Baltimore, *Cell,* 41:885, 1985.
Grunhaus and Horwitz, *Seminar in Virology,* 3:237-252, 1992.
Harland and Weintraub, *J Cell Biol.,* 101(3):1094-1099, 1985.
Haslinger and Karin, *Proc. Natl. Acad. Sci. USA,* 82:8572, 1985.
Hauber and Cullen, *J Virology,* 62:673, 1988.
Hen et al., *Nature,* 321:249, 1986.
Hensel et al., *Lymphokine Res.,* 8:347, 1989.
Hermonat and Muzycska, *Proc. Natl. Acad. Sci. USA,* 81:6466-6470, 1984.
Herr and Clarke, *Cell,* 45:461, 1986.
Hersdorffer et al., *DNA Cell Biol.,* 9:713-723, 1990.
Herz and Gerard, *Proc. Natl. Acad. Sci. USA,* 90:2812-2816, 1993.
Hill et al., *Circulation,* 101:2863-2869, 2000.
Hirochika et al., *J Virol.,* 61:2599, 1987.
Hirsch et al., *Mol. Cell. Biol.,* 10:1959, 1990.
Holbrook et al., *Virology,* 157:211, 1987.
Horlick and Benfield, *Mol. Cell. Biol.,* 9:2396, 1989.
Horwich et al. *J. Virol.,* 64:642-650, 1990.
Huang et al., *Cell,* 27:245, 1981.
Hug et al., *Mol. Cell. Biol.,* 8:3065, 1988.
Hutvagner et al., *PLoS Biol.,* 2(4):E98, 2004.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Ito and Roeder, *Trends Endocrinol. Metab.,* 12:127-134, 2001.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Mol. Cell. Biol.,* 9:3393, 1989.
Jones and Shenk, *Cell,* 13:181-188, 1978.
Kadesch and Berg, *Mol. Cell. Biol.,* 6:2593, 1986.
Kaneda et al., *Science,* 243:375-378, 1989.
Karin et al., *Mol. Cell. Biol.,* 7:606, 1987.
Karin et al., *Mol. Cell. Biol.,* 7:606, 1987.
Karlsson et al., *EMBO J.,* 5:2377-2385, 1986.
Katinka et al., *Cell,* 20:393, 1980.
Katinka et al., *Nature,* 290:720, 1981.
Kato et al., *J. Biol. Chem.,* 266:3361-3364, 1991.
Kawamoto et al., *Mol. Cell. Biol.,* 8:267, 1988.

Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Kinugawa et al., *Circ. Res.*, 89:591-598, 2001.
Kinugawa et al., *J. Clin. Endocrinol. Metab.*, 86:5089-5090, 2001.
Kiriazis and Kranias, *Annu. Rev. Physiol.*, 62:321-351, 2000.
Klamut et al., *Mol. Cell. Biol.*, 10: 193, 1990.
Klein et al., *Nature*, 327:70-73, 1987.
Koch et al., *Mol. Cell. Biol.*, 9:303, 1989.
Krek et al., *Nature Genetics*, 37:495-500, 2005.
Krenz and Robbins, *J Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Kriitzfeldt et al., *Nature*, 438:685-689, 2005.
Kuhl et al., *Cell*, 50:1057, 1987.
Kunz et al., *Nucl. Acids Res.*, 17:1121, 1989.
Lagos-Quintana et al., *Science*, 294(5543):853-858, 2001.
LaPointe et al., *Hypertension* 27(3 Pt 2):715-22, 1996.
LaPointe et al., *J Biol. Chem.*, 263(19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Le Gal La Salle et al., *Science*, 259:988-990, 1993.
Lee and Ambros, *Science*, 294(5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lin et al., *Mol. Cell. Biol.*, 10:850, 1990.
Liu et al., *Proc Natl Acad Sci USA* 101:9740-9744, 2004.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Samow, *Nature*, 353:90-94, 1991.
Majors and Varmus, *Proc. Natl. Acad. Sci. USA*, 80:5866, 1983.
Mann et al., *Cell*, 33:153-159, 1983.
Mansen et al., *Mol. Endocrinol.*, 15:2106-2114, 2001.
Markowitz et al., *J. Virol.*, 62:1120-1124, 1988.
McNeall et al., *Gene*, 76:81, 1989.
Meister and Tuschl, *Nature*, 431:343-9, 2004.
Miksicek et al., *Cell*, 46:203, 1986.
Molkentin et al., *Cell* 93:215-228, 1998.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271(49):31688-31694, 1996.
Muesing et al., *Cell*, 48:691, 1987.
Naya et al., *J Biol. Chem.*, 275(7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721: 185-190, 1982.
Nicolau et al., *Methods Enzymol.*, 149:157-176, 1987.
Ojamaa et al., *Endocrinology*, 141:2139-2144, 2000.
Ondek et al., *EMBO J.*, 6:1017, 1987.
Ornitz et al., *Mol. Cell. Biol.*, 7:3466, 1987.
Palmiter et al., *Nature*, 300:611, 1982.
Pantos et al., *Horm. Metab. Res.*, 38:308-313, 2006.
Park et al., *Mol. Cell.*, 19:643-653, 2005.
Paskind et al., *Virology*, 67:242-248, 1975.
Pasquinelli and Ruvkun, *Ann. Rev. Cell Dev. Biol.*, 18:495-513, 2002.
Pavri et al., *Mol. Cell.*, 18:83-96, 2005.
PCT Appln. WO 0071096
PCT Appln. WO 84/03564
PCT Appln. WO 98/33791
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10: 1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9: 169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1985.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2: 1144, 1988.
Sambrook and Russell, Molecular Cloning: A Laboratory Manual 3rd Ed., Cold Spring Harbor Laboratory Press, 2001.
Satake et al., *J Virology*, 62:970, 1988.
Schaffner et al., *J Mol. Biol.*, 201:81, 1988.
Schuyler and Yarbrough, *Basic Res. Cardiol.*, 85:481-494, 1990.
Searle et al., *Mol. Cell. Biol.*, 5:1480, 1985.
Sempere et al., *Genome Biol.*, 5:R13, 2004.
Sharp and Marciniak, *Cell*, 59:229, 1989.
Shaul and Ben-Levy, *EMBO J*, 6:1913, 1987.
Sherman et al., *Mol. Cell. Biol.*, 9:50, 1989.
Shingara et al., *RNA* 11:1461-1470, 2005.
Sleigh and Lockett, *J EMBO*, 4:3831, 1985.
Spalholz et al., *Cell*, 42:183, 1985.
Spandau and Lee, *J Virology*, 62:427, 1988.
Spandidos and Wilkie, *EMBO J*, 2:1193, 1983.
Stephens and Hentschel, *Biochem. J*, 248:1, 1987.

Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J Virology*, 62:614, 1988.
Top et al., *J Infect. Dis.*, 124:155-160, 1971.
Treisman, *Cell*, 46(4):567-174, 1986
Tronche et al., *Mol. Biol. Med.*, 7:173, 1990.
Tronche et al., *Mol. Cell. Biol.*, 9(11):4759-4766, 1989.
Trudel and Constantini, *Genes and Dev.*, 6:954, 1987.
Tsika et al., *Am. J Physiol. Cell Physiol.*, 283:C1761-C1775, 2002.
Tur-Kaspa et al., *Mol. Cell. Biol.*, 6:716-718, 1986.
Tyndell et al., *Nuc. Acids. Res.*, 9:6231, 1981.
Vadaszova et al., *Physiol. Res.* 53(1):S57-61, 2004.
van Rooij et al., *Proc. Natl. Acad. Sci. USA*, 103(48):18255-18260, 2006.
Vannice and Levinson, *J Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Wei et al., *J Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J Biol. Chem.*, 262:4429-4432, 1987.
Xu et al., *Curr. Biol.*, 13:790-795, 2003.
Yamauchi-Takihara et al., *Proc. Natl. Acad. Sci. USA*, 86(10): 3504-3508, 1989.
Yang and Russell, *Proc. Natl. Acad. Sci. USA*, 87:4144-4148, 1990.
Yao and Eghbali, *Circ. Res.* 71:831-839, 1992.
Young et al., In: *Handbook of Applied Therapeutics*, 7.1-7.12 and 9.1-9.10, 1989.
Yutzey et al. *Mol. Cell. Biol.*, 9:1397, 1989.
Zelenin et al., *FEBS Lett.*, 287(1-2):118-120, 1991.
Zeng et al., *Cancer Res.*, 62(13):3630-3635, 2002.
Ziober and Kramer, *J Biol. Chem.*, 271(37):22915-22, 1996.

What is claimed is:

1. A method for identifying a subject in need of treatment for a denervating neuropathic state comprising:
   (a) assessing neuromuscular junction stability in a subject;
   (b) obtaining a skeletal muscle tissue sample from said subject and assessing expression of miR-206 in the tissue sample;
   wherein decreased neuromuscular junction stability and an elevated expression level of miR-206 indicate that the subject is in need of treatment for a denervating neuropathic state.

2. The method of claim 1, wherein the subject is suspected of having a denervating neuropathic state selected from the group consisting of spinal cord injury, peripheral nerve injury, myasthenia gravis, amyotrophic lateral sclerosis, Friedreich's ataxia, spinal muscular atrophy, and spinocerebellar ataxia.

3. The method of claim 1, further comprising assessing the expression of one or more genes regulated by miR-206 in the tissue sample, wherein one or more genes regulated by miR-206 is HDAC4, Dach2, or myogenin.

4. The method of claim 1, wherein the elevated expression level of miR-206 is determined by comparing the expression of miR-206 in said sample to the expression of miR-206 in a normal skeletal muscle tissue sample.

5. The method of claim 1, wherein an elevated expression level of miR-206 is indicative of denervated skeletal muscle.

6. The method of claim 1, further comprising assessing expression of miR-133b in said skeletal muscle tissue sample from the subject, wherein an elevated expression level of miR-133b indicates that the subject is in need of treatment for a denervating neuropathic state.

7. The method of claim 1, further comprising assessing expression of miR-1 and/or miR-133a in said skeletal muscle tissue sample from the subject, wherein a reduced expression level of miR-1 and/or miR-133a indicates that the subject is in need of treatment for a denervating neuropathic state.

8. The method of claim 1, wherein assessing miR-206 expression comprises measuring the miR-206 expression level by Northern blotting or real-time polymerase chain reaction.

9. The method of claim 1, wherein miR-206 comprises a sequence of SEQ ID NO: 2.

10. The method of claim 1, wherein the elevated expression level of miR-206 is greater than 2-fold.

11. The method of claim 1, wherein the elevated expression level of miR-206 is about 9-fold.

12. The method of claim 6, wherein miR-133b comprises a sequence of SEQ ID NO: 8.

13. The method of claim 6, wherein the elevated expression level of miR-133b is greater than 2-fold.

14. The method of claim 7, wherein miR-1 comprises a sequence of SEQ ID NO: 4.

15. The method of claim 7, wherein miR-133a comprises a sequence of SEQ ID NO: 6.

16. The method of claim 7, wherein the reduced expression level of miR-1 and/or miR-133a is at least 2-fold.

* * * * *